US010506927B2

(12) United States Patent
Melodia et al.

(10) Patent No.: US 10,506,927 B2
(45) Date of Patent: Dec. 17, 2019

(54) MEDIUM-ACCESS CONTROL SCHEMES FOR ULTRASONIC COMMUNICATIONS IN THE BODY BASED ON SECOND ORDER STATISTICS

(71) Applicant: The Research Foundation for The State University of New York, Amherst, NY (US)

(72) Inventors: Tommaso Melodia, Newton, MA (US); Zhangyu Guan, Boston, MA (US); Giuseppe Enrico Santagati, Cambridge, MA (US)

(73) Assignee: The Research Foundation for The State University of New York, Amherst, NY (US)

( * ) Notice: Subject to any disclaimer, the term of this patent is extended or adjusted under 35 U.S.C. 154(b) by 722 days.

(21) Appl. No.: 15/025,627

(22) PCT Filed: Sep. 30, 2014

(86) PCT No.: PCT/US2014/058486
§ 371 (c)(1),
(2) Date: Mar. 29, 2016

(87) PCT Pub. No.: WO2015/048815
PCT Pub. Date: Apr. 2, 2015

(65) Prior Publication Data
US 2016/0235302 A1 Aug. 18, 2016

Related U.S. Application Data

(60) Provisional application No. 61/884,358, filed on Sep. 30, 2013.

(51) Int. Cl.
*H04B 17/15* (2015.01)
*A61B 5/00* (2006.01)
*H04B 11/00* (2006.01)

(52) U.S. Cl.
CPC .......... *A61B 5/0028* (2013.01); *A61B 5/0024* (2013.01); *A61B 5/0031* (2013.01);
(Continued)

(58) Field of Classification Search
CPC ....... A61B 5/00; A61B 5/0015; A61B 5/0024; A61B 5/0028; A61B 5/0031;
(Continued)

(56) References Cited

U.S. PATENT DOCUMENTS 4,045,767 A 8/1977 Nishihara et al.
4,982,339 A * 1/1991 Insana .................. A61B 8/00
 600/437

(Continued)

FOREIGN PATENT DOCUMENTS

WO 2013168170 11/2013

OTHER PUBLICATIONS

Galluccio, et al., Challenges and Implications of Using Ultrasonic Communications in Intra-body Area Networks, 2012 9th Annual Conference on Wireless On-Demand Network Systems and Services Jan. 1, 2012.

(Continued)

*Primary Examiner* — Isam A Alsomiri
*Assistant Examiner* — Amie M Ndure
(74) *Attorney, Agent, or Firm* — Hodgson Russ LLP

(57) ABSTRACT

Methods for ultrasonic communications through biological tissue using ultrasonic pulses are disclosed. For example, methods for calculating a forward data generation rate and a forward transmission probability profile for ultrasonic communications through biological material are disclosed. The method may comprise measuring sets interference values corresponding to instants on a communication channel. First and second order moments may be calculated for each instant based on the measured interference values. An out-
(Continued)

age probability may be calculated for each set and the forward data generation rate and forward transmission probability profile may be calculated based on the outage probability value and other parameters and a threshold transmission rate, a transmission delay threshold, and a residual transmission error rate.

16 Claims, 11 Drawing Sheets

(52) U.S. Cl.
CPC .......... *A61B 5/7203* (2013.01); *A61B 5/7225* (2013.01); *H04B 11/00* (2013.01); *H04B 17/15* (2015.01)

(58) Field of Classification Search
CPC ... A61B 5/7203; A61B 5/7225; A61B 5/0205; A61B 5/14532; H04B 11/00; H04B 17/15; A61M 5/14242
See application file for complete search history.

(56) References Cited

U.S. PATENT DOCUMENTS

| | | | |
|---|---|---|---|
| 6,056,695 A | 5/2000 | Rupp et al. | |
| 7,822,804 B2* | 10/2010 | Lee | H04W 4/02 709/202 |
| 7,945,064 B2 | 5/2011 | O'Brien, Jr. et al. | |
| 8,103,241 B2* | 1/2012 | Young | A61B 5/0002 455/404.1 |
| 8,159,353 B2* | 4/2012 | Laukkanen | A61B 5/1118 128/903 |
| 8,214,082 B2* | 7/2012 | Tsai | G06F 19/3418 700/253 |
| 8,308,482 B2* | 11/2012 | Pearce | A61N 1/0484 434/11 |
| 8,422,337 B2 | 4/2013 | Su et al. | |
| 8,512,241 B2 | 8/2013 | Bandy et al. | |
| 8,626,296 B2 | 1/2014 | Von Arx et al. | |
| 2008/0001735 A1* | 1/2008 | Tran | G06F 19/3418 340/539.22 |
| 2010/0256493 A1 | 10/2010 | Chono | |
| 2010/0298669 A1 | 11/2010 | Ida | |
| 2012/0130246 A1 | 5/2012 | Haider et al. | |
| 2013/0072794 A1 | 3/2013 | Waki | |
| 2013/0197320 A1 | 8/2013 | Albert et al. | |
| 2014/0050321 A1 | 2/2014 | Albert et al. | |
| 2018/0049675 A1* | 2/2018 | Kerber | A61B 5/0205 |

OTHER PUBLICATIONS

Santagati, et al., Opto-ultrasonic communications for wireless intra-body nanonetworks, Nano Communication Networks, vol. 5, 2014, pp. 3-14 Mar. 12, 2014.

Santagati, et al., Distributed MAC and Rate Adaptation for Ultrasonically Networked Implantable Sensors,Sensor, Mesh and Ad Hoc Communications and Networks, 2013 10th Annual IEEE Communications Society Confererece, http://arxiv.org/pdf/1302.0897.pdf Feb. 6, 2013.

* cited by examiner

MEDIUM-ACCESS CONTROL SCHEMES FOR ULTRASONIC COMMUNICATIONS IN THE BODY BASED ON SECOND ORDER STATISTICS

CROSS-REFERENCE TO RELATED APPLICATIONS

This application claims priority to U.S. Provisional Application No. 61/884,358, filed on Sep. 30, 2013, the disclosure of which is incorporated herein by reference.

STATEMENT REGARDING FEDERALLY SPONSORED RESEARCH

This invention was made with government support under grant no. CNS1253309 awarded by the National Science Foundation. The government has certain rights in the invention.

FIELD OF THE INVENTION

The invention relates to systems and methods for communication through biological tissue. For example, systems and methods for transmitting and receiving ultrasonic communications through biological tissue.

BACKGROUND OF THE INVENTION

Body area networks have received considerable attention in the last five years, driven by the fascinating promise of a future where carefully engineered miniaturized biomedical devices implanted, ingested or worn by humans can be wirelessly internetworked to collect diagnostic information (e.g., measure the level of glucose in the blood of diabetic patients) and to fine-tune medical treatments (e.g., adaptively regulate the dose of insulin administered) over extended periods of time.

One obstacle of enabling this vision of networked implantable devices is posed by the physical nature of propagation in the human body, which is composed primarily (65%) of water, a medium through which RF electromagnetic waves hardly propagate, even at relatively low frequencies. Most research in body area networks to date has focused on traditional RF communications along the body surface. Accordingly, most research has focused on reducing the radiated power to avoid overheating of tissues. The core challenge of enabling networked intra-body communications through body tissues is substantially unaddressed.

Acoustic waves, typically generated through piezoelectric materials, are known to propagate better than their RF counterparts in media composed mainly of water. Since World War II, piezoelectrically generated acoustic waves have found application, among others, in underwater communications (typically at frequencies between 0 and 100 kHz), in indoor localization in sensor networks, and, massively, in ultrasonic medical imaging.

While communication at low frequencies requires sizable transducers, innovations in piezoelectric materials and fabrication methods, primarily driven by the need for resolution in medical imaging, have made micro and nano scale transducers a reality. Moreover, the medical experience of the last decades has demonstrated that ultrasound is fundamentally safe, as long as acoustic power dissipation in tissue is limited to specific safety levels. Ultrasonic wave heat dissipation in tissues is minimal compared to RF waves.

A major challenge to using ultrasonic waves for communication is the temporal and spatial uncertainty that characterizes ultrasonic interference generated by devices in the human body and denser deployment in specific areas (e.g., heart or brain). The temporal uncertainty of interference is caused by asynchronous transmissions of different devices and time-varying ultrasonic communication channels. Moreover, the distance-dependent propagation delay of ultrasonic signals generates spatial uncertainty in interference. For example, acoustic signals simultaneously transmitted by different nodes located at different distances from an intended receiver, or different multipath replicas of the same signal, do not necessarily reach the receiver at the same time.

Cross-layer optimization algorithms for wireless networks exist. However, algorithms designed for RF wireless communications are not designed for the spatially and temporally uncertain ultrasonic environment. In addition, these RF algorithms often require coordination and message exchanges that are not desirable in this environment.

Recent efforts have attempted to address some of the challenges of interference modeling at the MAC layer. For example, with slotted transmission the packet collision probability can be reduced by adding a guard band to each time slot to limit the effect of the spatial uncertainty of interference. However, these solutions mainly rely on signaling exchanges that still suffer from the low-speed of sound, result in under-utilization of the channel, and therefore suffer from low throughput. Furthermore, these solutions look at the problem from a medium access control (MAC) perspective, exclusively. In addition, previous solutions are largely based on the protocol interference model (i.e., a packet is lost whenever two transmissions overlap at a receiver) which is not the case with ultrasonic intra-body transmission schemes. Ultimately, existing models fail to capture the statistical behavior of time-varying and spatially uncertain ultrasonic channels.

BRIEF SUMMARY OF THE INVENTION

Control schemes for ultrasonic communication in biological tissue are disclosed. One embodiment of the present invention is a method for calculating a forward data generation rate and a forward transmission probability profile. The method comprises the step of measuring, with a receiver, sets of interference values between the receiver and a transmitter. The interference values may be measured at uniformly spaced instants. The interference values may be a measurement of power. Noise may be a component of the interference values. Each set of interference values may correspond to one or more instants in a time slot on a communication channel.

The method may further comprise the step of calculating a first order moment and a second order moment for each instant based on the interference values corresponding to the measured instant. The method may further comprise the step of calculating an outage probability value for each set. The method may further comprise calculating the forward data generation rate and the forward transmission probability profile based on the calculated outage probability value and a threshold transmission rate, a transmission delay threshold, and a residual transmission error rate. The threshold transmission rate, transmission delay threshold, and residual transmission error rate may be predetermined. The forward data generation rate and the forward transmission probability profiles may be calculated using log-convex optimization.

In one embodiment, the method may further comprise the step of grouping consecutive interference values within each set. The consecutive interference values may be grouped such that the temporal correlation coefficient between any two values in each group is greater than a temporal correlation threshold. The temporal correlation threshold may be estimated based on packet drop rate.

The consecutive interference values may be grouped to contain the maximum number of instants. In such an embodiment, the first order moment and the second order moment may be calculated for each group based on the interference values corresponding to the group. In addition, the outage probability value for each set may be calculated based on the calculated first and second order moments of the groups in the set or the moments of each measured instant.

In another embodiment, the method may further comprise the step of sending, to a transmitter, the forward data generation rate and the forward transmission probability profile. In one embodiment, the method may further comprise receiving data, from the transmitter, using the forward data generation rate and the forward transmission probability profile. The receiver may perform an action based on the received data.

In one embodiment, the forward data generation rate and the forward transmission probability profile may be sent in a data packet comprising an identifier of the intended transmitter, the forward data generation rate, and the forward transmission probability profile.

In one embodiment, the receiver may be a transceiver. In such an embodiment, the method may further comprise transmitting data using the forward data generation rate and the forward transmission probability profile.

In another embodiment, the method may further comprise the step of setting a random data generation rate and transmission probability profile for each time slot and communication channel and transmitting data at the randomly set data generation rate and transmission probability profile. In such an embodiment, the setting and transmitting steps may occur prior to the measuring steps.

In one embodiment, the method may further comprise recording the sets of interference values in a memory of the receiver. In another embodiment, the steps of the method are performed using a processor of the receiver.

The invention can also be embodied as a method of MAC for an ultrasonic body area network (BAN) or body surface network (BSN). The invention can also be embodied as a system comprising a plurality of sensor nodes operating according to the methods described herein. The nodes may be transmitter-receiver pairs or transceivers. In a transmitter-receiver pair or a transceiver, the receiver may measure and send the collected channel state information (CSI) to a transmitter. The transmitter may transmit the data to a receiver, and the receiver may send the data to an external monitoring device or actuator. The invention may also be embodied as a non-transitory computer-readable medium having stored thereon computer executable code, which, when executed, causes a specially configured computer system to perform methods of the present invention.

Certain embodiments of the present invention can work with a broad range of physical (PHY) layers. Generally, PHY layers include all communication functionalities needed to carry information bits over a wireless link. The PHY layer can be based on a broad range of different modulation and channel coding schemes. As for modulation, frequency, phase, and amplitude modulation schemes can be used. For example, if phase modulation is adopted, the transmitter emits a signal with 0-degree initial phase when transmitting 1, and 180-degree initial phase when transmitting 0. For channel coding, the PHY layer may adopt block coding, turbo coding, and low-density parity-check code (LDPC), among others.

The present invention may optimize network control strategies for implantable devices interconnected through ultrasonic waves. Some embodiments of the invention utilize lightweight, asynchronous, and distributed algorithms for joint rate control and stochastic channel access that optimize the performance of Ultrasonic Intra-Body Area Networks (U-IBANs).

Disclosed are algorithms for cross-layer control of functionalities at different layers of the networking protocol stack in ultrasonic networks. In addition, one embodiment of the present invention comprises methods of resource allocation to jointly control different networking functionalities of devices in an ultrasonic network (e.g., channel access, spectrum management, queuing, and rate control). These methods may optimize network throughput with a constrained energy budget, while keeping the radiated power within safe limits.

As used within, the term lightweight may refer to algorithms based on local decisions taken through polynomial-time algorithms and with minimal message exchange. The term asynchronous may refer to the updates at different nodes being unsynchronized. The term distributed may refer to a network without a centralized entity.

Statistical models of the spatial and temporal variability of ultrasonic interference are disclosed. One such statistical model, referred to herein as M-sampling, captures the effects of unaligned interference. M-sampling characterizes interference through a vector of measurements taken at multiple instants of time at each receiver during a given interval (i.e., time slot). In addition, the effects of temporal uncertainty (i.e., the random transmission of different nodes on time-varying ultrasonic channels) on the interference level at each measurement point may be modeled using Nakagami probability distribution functions.

An optimization framework may be developed based on the statistical model. One possible objective of the framework is to maximize the throughput achievable by nodes that can control their transmission profile (i.e., the probability to transmit over a series of time slots and available channels) and maximize data generation rate under energy budget constraints.

Probabilistic, throughput-maximizing, distributed cross-layer control strategies are disclosed within, based on the developed stochastic models of ultrasonic interference.

As used within, |•| represents cardinality of a set, P[•] represents the probability an event occurs; E[•] and D[•] denote expectation and variance of a random variable.

One embodiment of the present invention comprises a fully distributed solution algorithm. Another embodiment of the present invention comprises a centralized (but globally optimal) solution algorithm to provide an upper-bound performance benchmark. Through extensive simulation, some embodiments of the present invention achieve considerable throughput gain, up to 9× for example, compared with traditional algorithms.

DESCRIPTION OF THE DRAWINGS

For a fuller understanding of the nature and objects of the invention, reference should be made to the following detailed description taken in conjunction with the accompanying drawings, in which.

DETAILED DESCRIPTION OF THE INVENTION

Throughout the application, the term "transmitter-receiver pairs" includes transceivers.

Ultrasonic Propagation in Tissues

Ultrasonic waves originate from the propagation of mechanical vibrations of particles in an elastic medium at frequencies above the upper limit for human hearing, i.e., 20 kHz. Even if each particle oscillates around its rest position, the vibration energy propagates as a wave traveling from particle to particle through the material. Acoustic propagation through a medium is governed by the acoustic wave equation (referred to as the Helmhotz equation), which describes pressure variation over the three dimensions, $$\nabla^2 P - \frac{1}{c^2}\frac{\partial^2 p}{\partial t^2} = 0,$$

where P(x, y, z, t) represents the acoustic pressure scalar field in space and time, and c is the propagation speed in the medium with a typical value of 1500 m/s in blood (i.e., five orders of magnitude slower than RF propagation in air).

Attenuation can be significant and attenuation increases with the distance between transmitter and receiver. Moreover, the beam spread is inversely proportional to the ratio between the diameter of the radiating surface and the wavelength of the operating frequency. Consequently, since most biomedical sensing applications require directional transducers, one needs to operate at high frequencies to keep the transducer size small. However, as expected, higher frequencies lead to higher attenuation.

TABLE 1

| Frequency Limits for A = 100 dB | | |
|---|---|---|
| Communication Range | Distance | Frequency Limit |
| Short Range | μm-mm | >1 GHz |
| Medium Range | mm-cm | ≅100 MHz |
| Long Range | >cm | ≅10 MHz |

Table 1 shows the maximum "allowed" carrier frequency for a 100 dB maximum tolerable attenuation. Even with transmission distances of no more than a few tens of centimeters, due to the low speed of ultrasonic signals, the propagation delay can be rather large compared with the channel access period, leading to non-aligned interference and thus making time-division MAC schemes not directly applicable.

Figure 1:
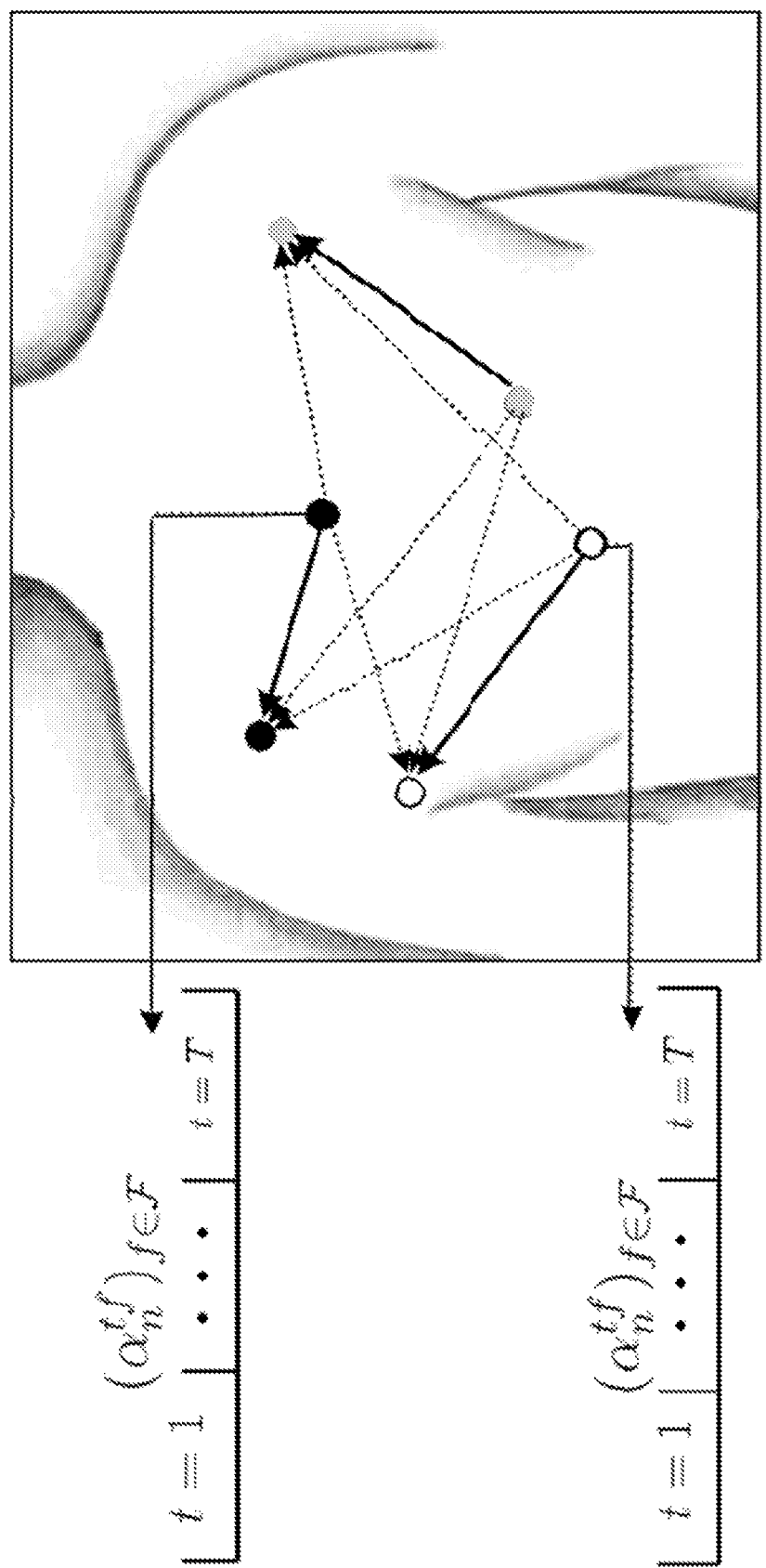
FIG. 1 is a diagram of an Ultrasonic IntraBody Area Network (U-IBAN) according to one embodiment of the present invention.

In FIG. 1, each dot represents a transmitter or a receiver. The solid lines represent signal links. The dashed lines represent interfering links. FIG. 1 shows a U-IBAN with a set $\mathcal{N}$ of concurrent sessions with $|\mathcal{N}|=N$, each comprising of a transmitter-receiver pair. The available spectrum is divided into a set $\mathcal{F}$ of orthogonal sub-channels with $|\mathcal{F}|=F$. The latter can be obtained on a code-division or frequency-division basis. Transmission time is divided into consecutive time slots, which are further grouped into consecutive frames each consisting of a set $\mathcal{T}$ of time slots with $|\mathcal{T}|=T$.

Let $R=(R_n)_{n\in\mathcal{N}}$ represent the data generation profile, i.e., the transport-layer data allowed in the network. Each source node $n\in\mathcal{N}$ introduces data in its queue at an average rate of $R_n$ [bit/s]. Because of the fast variability and high propagation delay of the ultrasonic channel, each session can obtain only statistical channel state information (CSI) at the transmitter side (i.e., no fast feedback is available). Therefore, each transmitter adopts a stochastic policy to decide whether to transmit in a specific time slot and over which sub-channel to transmit. Let $\alpha_n^t=(\alpha_n^{tf})_{f\in\mathcal{F}}$ denote the data transmission vector of transmitter $n\in\mathcal{N}$ in time slot $t\in\mathcal{T}$ where $\alpha_n^{tf}$ represents the probability that session n transmits a packet over sub-channel $f\in\mathcal{F}$. The transmission profile of session $n\in\mathcal{N}$ in a time frame denoted as $\alpha_n$ can be written as $\alpha_n=(\alpha_n^t)_{t\in\mathcal{T}}$. Let $\alpha$ represent the transmission profile of all sessions in $\mathcal{N}$ and $\alpha_{-n}$ represent the transmission policy vector of all sessions except n. As such, $\alpha$ and $\alpha_{-n}$ can be written as $\alpha=(\alpha_n)_{n\in\mathcal{N}}$ and $\alpha_{-n}=(\alpha_m))_{m\in\mathcal{N}/n}$, respectively. This model includes deterministic policies (i.e., in which the probability to transmit over a specific time slot or channel is equal to one) as a special case.

Let $P_n^0$ denote the transmission power of user $n\in\mathcal{N}$. $T_{slt}$ represents the time slot duration and $E_n^{max}$ is the maximum energy available in each time frame consisting of $|\mathcal{T}|=T$ consecutive time slots. As such, $$\alpha_n^{tf}\geq 0, \forall n\in\mathcal{N}, t\in\mathcal{T}, \forall f\in\mathcal{F} \quad (1)$$

$$\alpha_n^{tf}\leq 1, \forall n\in\mathcal{N}, \forall t\in\mathcal{T}, \forall f\in\mathcal{F} \quad (2)$$

$$\Sigma_{f\in\mathcal{F}}\,\alpha_n^{tf}\leq 1, \forall n\in\mathcal{N}, \forall t\in\mathcal{T} \quad (3)$$

$$\Sigma_{t\in\mathcal{T}}(R_n g\pm E_n^0+\Sigma_{f\in\mathcal{F}}\alpha n^{tf}P_n^0)T_{slt}\leq E_n^{max}, \forall n\in\mathcal{N}\,t\in\mathcal{T} \quad (4)$$

where $E_n^0$ represents the energy [J] consumed by source node n to generate and process (e.g., A/D conversion, source encoding, etc.) one bit of data. Constraint (4) imposes a balance between the energy needed for (i) data processing and generation and (ii) transmission for throughput maximization, under a given energy budget and limiting radiation to safe levels. It is advantageous to incorporate rate control into the optimization framework, since in some scenarios of interest, it might be very difficult to determine the optimal rate in advance. Consider for example a dynamic U-IBAN with a set of miniaturized sensors cruising along the blood vessels to conduct multi-site measurement of physiological quantities of interest. As illustrated in the Simulation Results section below, without rate control, trivially allocating too high a portion of the energy budget to data generation leads to growing queueing delay that could result in high packet drop rates (therefore reducing the throughput). The underlying queueing model will be introduced in the Interference Model & Throughput Derivation section below.

Interference Model & Throughput Derivation

To model the interference affecting ultrasonic communications in intra-body environments, the underlying fading channels should be characterized.

Channel Model.

Transmission power may be fixed since power control requires instantaneous CSI at the transmitter, which is assumed to be unavailable. Let $h_{nm}^{tf}$ denote the channel gain of the link from transmitter m to receiver n on subchannel $f \in \mathcal{F}$ at time slot t. For ultrasonic propagation in tissues, $h_{nm}^{tf}$ can be represented as:

$$h_{nm}^{tf} = H_{nm}^{f} \cdot (\rho_t)^2 \quad (5)$$

where $\rho_t$ indicates the channel fading coefficient, while $H_{nm}^{f}$ represents the transmission attenuation that an ultrasonic signal transmitted on sub-channel $f \in \mathcal{F}$ experiences over a transmission distance $d_{nm}$. CEN(f) is the central frequency of sub-channel f. $H_{nm}^{f}$ can be represented as $H_{nm}^{f} = e^{-\beta(CEN(f)) \cdot d_{nm}}$, where $\beta(CEN(f))$ (in [np·cm$^{-1}$]) represents the amplitude attenuation coefficient that captures effects associated to energy dissipation from the ultrasonic beam. The parameter $\beta(CEN(f))$ can be further represented as $\beta = a \cdot (CEN(f))^b$, where a (in [np m$^{-1}$ MHz$^{-b}$]) and b are attenuation parameters characterizing the tissue. These parameters may be measured off-line or on-line (in vivo). The following terms are simplified for convenience: $h_{nm}^{tf}$ $H_{nm}^{f}$ and $d_{nm}$ to $h_{n}^{tf}$, $H_{n}^{f}$ and $d_n$, respectively, for n=m.

Since the human body is composed of different organs and tissues each having different sizes, densities and sound speeds, and due to constant blood flow and tissue agitation, signal propagation in U-IBANs is deeply affected by time-varying multipath fading and scattering. Therefore, the channel fading coefficient $\rho_t$ in (5) can be statistically characterized using a Nakagami distribution function $\xi(x)$, $$\xi(x) = P[\rho_t = x] = \frac{2 s z^z x^{2sz-1}}{\Gamma(z) \Omega^z} e^{-\frac{z}{\Omega} x^{2s}} \quad (6)$$

where $\omega$ and $\Omega$ are the shaping and spreading parameters of the Nakagami distribution function that can be measured off-line or estimated on-line (in vivo), and $\Gamma(\omega) \triangleq \int_0^\infty x^{\omega-1} e^{-x}$ dx is the gamma function.

Interference Model.

The interference experienced at each receiver not only depends on the channel model described above, but also depends on the interfering concurrent transmissions of the other nodes. Specifically, because of the non-negligible ultrasonic propagation delay, which can possibly be much larger than the time duration of a time slot, signals transmitted simultaneously by different transmitters do not in general reach a receiver at the same time. This makes interference modeling for intra-body ultrasonic networks rather challenging.

Figure 2:
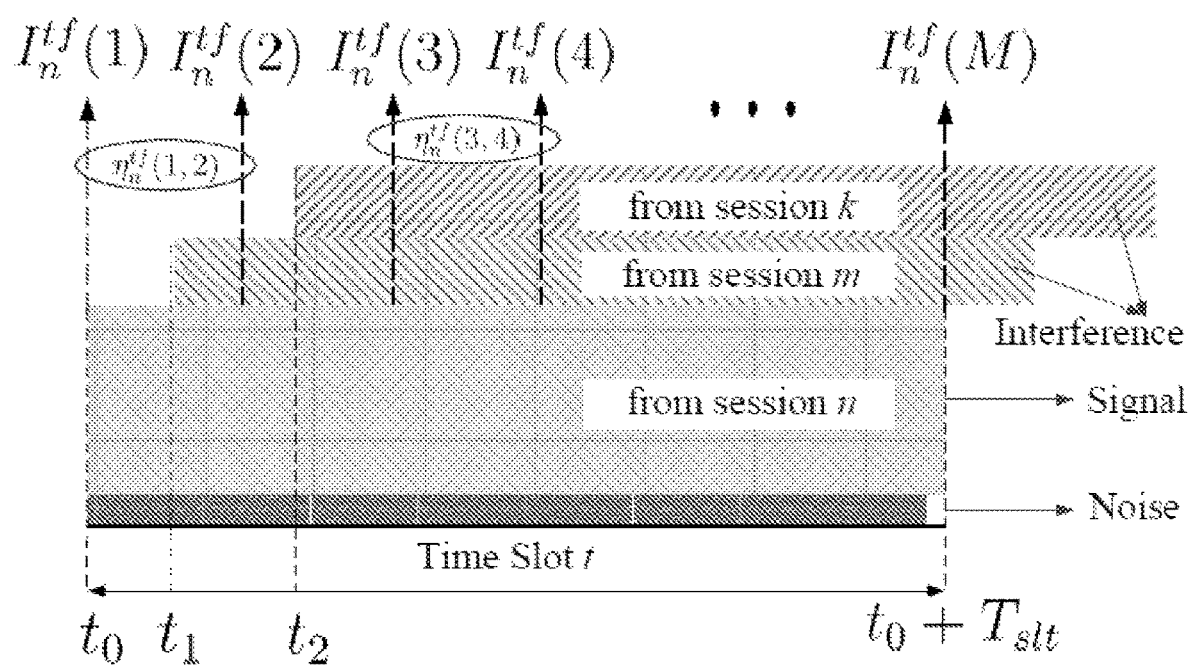
FIG. 2 is an illustration of an M-sampling method according to one embodiment of the present invention.

To model the effect of non-aligned interference, the M-sampling method can be used. This method characterizes interference through a vector of measurements taken at multiple instants of time at each receiver during a given interval (i.e., time slot). Each receiver $n \in \mathcal{N}$ measures the received signal on each sub-channel $f \in \mathcal{F}$ in each time slot t at a set $\mathcal{M}_n^{tf}$ with $|\mathcal{M}_n^{tf}| = M$ of time instants. An illustration of the method is shown in FIG. 2.

Because of the non-aligned nature of interference, a signal from session $n \in \mathcal{N}$ that arrives at its intended receiver at the l-th measurement instant in time slot t, with $l \in \mathcal{M}_n^{tf}$ for any $f \in \mathcal{F}$, can be interfered by the transmission of any session $m \in \mathcal{N}/n$ occurring during time slot $\tilde{t}(m,n,t,l)$, which might be different from t. Denote the transmission probability corresponding to $\tilde{t}(m,n,t,l)$ as $\alpha_m^{\tilde{t}(m,n,t,l)f}$ (also $\alpha_m^{tf}(n,t,l)$ for notational convenience). Let $I_n^{tf}(l)$, $l \in \mathcal{M}_n^{tf}$ denote the aggregate interference measured by the receiver node of session $n \in \mathcal{N}$ on sub-channel $f \in \mathcal{F}$ at the l-th measurement point in time slot t. $I_n^{tf}(l)$ can be expressed as $$I_n^{tf}(l) = \sum_{m \in \mathcal{N}/n} P_m^0 h_{nm}^{tf} \hat{\alpha}_m^{tf}(n,t,l), \forall l \in \mathcal{M}_n^{tf} \quad (7)$$

where $\hat{\alpha}_m^{tf}(n,t,l) = 1$ with probability $\alpha_m^{tf}(n,t,l)$, and 0 with probability $1 - \alpha_m^{tf}(n,t,l)$.

Modeling the Temporal Correlation.

Since each transmission lasts for a time slot duration $T_{slt}$, measurements of aggregate interference at different time instants in each time slot could be closely correlated with each other. Let $\eta_n^{tf}(l, \tilde{l})$ with $l, \tilde{l} \in \mathcal{M}_n^{tf}$ represent the correlation coefficient between $I_n^{tf}(l)$ and $I_n^{tf}(\tilde{l})$. $\eta_n^{tf}(l, \tilde{l})$ can be expressed as $$\eta_n^{tf}(l, \tilde{l}) = \frac{E\left[(I_n^{tf}(l) - \mu_n^{tf}(l))(I_n^{tf}(\tilde{l}) - \mu_n^{tf}(\tilde{l}))\right]}{\sigma_n^{tf}(l) \sigma_n^{tf}(\tilde{l})} \quad (8)$$

where $\mu_n^{tf}(\cdot)$ and $\sigma_n^{tf}(\cdot)$ represent the mean and standard deviation of the corresponding interference measurement— their expressions will be given in the appendix below. The interference measurements in $\mathcal{M}_n^{tf}$ can be grouped into $\{\tilde{\mathcal{M}}_n^{tf}(l)\}$ with each $\tilde{\mathcal{M}}_n^{tf}(l)$ consisting of a subset of measurements starting from the l-th. A threshold-based grouping policy may be adopted, which groups a number of consecutive interference measurements $l, l+1, \ldots, \tilde{l}$ into $\tilde{\mathcal{M}}_n^{tf}(l)$ so that the correlation coefficient between the interference levels at any two measurements in the group (which are not necessarily adjacent to each other) is greater than a threshold denoted as $\eta_n^{th}$, i.e., $\eta_n^{tf}(l_1, l_2) \leq \eta_n^{th}$, $l \leq l_1, l_2 \leq \tilde{l}$. An example of the measurement grouping is shown in FIG. 2, where $I_n^{tf}(3)$ and $I_n^{tf}(4)$ are grouped together since $\eta_n^{tf}(3,4) > \eta_n^{th}$ while $I_n^{tf}(1)$ and $I_n^{tf}(2)$ are not.

The temporal correlation threshold can be either predetermined or estimated on-line (in vivo). In the latter case, a receiver node first initializes the threshold to a fixed value (e.g., 0.5), and then adjusts the threshold based on a comparison between the theoretically calculated outage probability (as will be described below) and the actual experienced packet drop rate. If the theoretical outage probability is higher, it means that the current threshold value is too high so that the channel randomness has been overestimated. In this case the receiver will reduce the correlation threshold by a fixed increment, e.g., by 0.01; likewise, the receiver may increase the threshold by a fixed value if the theoretical outage probability is lower than the experienced packet drop rate.

Throughput Derviation.

Based on the above interference model, a throughput expression may be derived for each session $n \in \mathcal{N}$. Due to the non-aligned interference as shown in FIG. 2, the experienced signal-to-interference-plus-noise ratio (SINR) in a time slot does not remain constant even if the channel is assumed to be slow fading. This results in a fast-fading channel in each time slot. This is different from a fast-fading channel in in-air RF communications, which is caused by the channel variation itself. Here, the fast fading is caused by the non-aligned interference. If the measurement instants in each time slot are uniformly spaced, then the outage probability of each session $n \in \mathcal{N}$ in time slot t over sub-channel $f \in \mathcal{F}$, denoted as $O_n^{tf}(\alpha_{-n})$, can be expressed as $$O_n^{tf}(\alpha_{-n}) \triangleq P\left[\sum_{l \in \mathcal{L}(\mathcal{M}_n^{tf})} \frac{|\tilde{\mathcal{M}}_n^{tf}(l)|}{|\mathcal{M}_n^{tf}|} C(n,t,f,l) < R_n^0\right] \quad (9)$$

where $\mathcal{L}(\mathcal{M}_n^{tf})$ represents the set of beginning measurements of each group in $\{\tilde{\mathcal{M}}_n^{tf}\}$ and $$C(n,t,f,l) = B \log_2(1 + P_n^0 h_n^{tf}/[(\delta_n^f)^2 + I_n^{tf}(l)]) \quad (10)$$

represents the achievable capacity during measurement group $\tilde{\mathcal{M}}_n^{tf}(l)$ with $(\delta_n^f)^2$ being the ambient noise power at the receiver node of session $n \in \mathcal{N}$ over sub-channel $f \in \mathcal{N}$; B represents the bandwidth [Hz] of each sub-channel, and $R_n^0$ is the target rate required to transmit a packet in a time slot. Then, the average capacity of session $n \in \mathcal{N}$, denoted as $C_n(\alpha_n, \alpha_{-n})$, can be expressed as $$C_n(\alpha_n, \alpha_{-n}) = \frac{1}{|\mathcal{T}|} \sum_{t \in \mathcal{T}} C_n^t(\alpha_n, \alpha_{-n}) m, \text{ with} \quad (11)$$

$$C_n^t(\alpha_n, \alpha_{-n}) = \sum_{f \in \mathcal{F}} \alpha_n^{tf}(1 - O_n^{tf}(\alpha_{-n})) R_n^0. \quad (12)$$

The outage probability value can also be estimated by measuring the currently experienced packet drop rate. For this purpose, a transmitter node may send a series of packets in consecutive time slots (e.g., 100). In the meanwhile, the intended receiver node decodes the received packets and keeps a record of the packets that have been received incorrectly because of transmission errors based on standard techniques, e.g., cyclic redundancy check. The resulting packet drop rate can then be fed back to the transmitter node as an estimate of the outage probability.

Finally, the packet arrivals of each user $n \in \mathcal{N}$ can be assumed to follow a Poisson process with average arrival rate $R_n$ [bit/s] and that the service time of each packet with length $L_n$ bits follows an exponential distribution, then the queue of each user $n \in \mathcal{N}$ can be modeled as an M/M/1 queue. Let $P_n^{dly}(R_n, \alpha_n, \alpha_{-n})$ represent the packet loss rate of user n caused by exceeding the maximum queueing delay $T_n^{th}$. Then, $P_n^{dly}(R_n, \alpha_n, \alpha_{-n})$ can be expressed as $$P_n^{dly}(R_n, \alpha_n, \alpha_{-n}) = e^{-(c_n(\alpha_n, \alpha_{-n}) - R_n)\frac{T_n^{th}}{L_n}}, \quad (13)$$

and the throughput of each session $n \in \mathcal{N}$, denoted as $U_n(R_n, \alpha_n, \alpha_{-n})$, can be expressed as $$U_n(R_n, \alpha_n, \alpha_{-n}) = R_n(1 - P_n^{dly}(R_n, \alpha) - P_n^{err}), \quad (14)$$

where $P_n^{err}$ represents the residual packet error rate due to non-perfect channel coding/decoding techniques, which is considered fixed herein.

As such an expression for the throughput can be derived for each session. One objective may be to maximize the sum throughput of all sessions in $\mathcal{N}$, by jointly adjusting the data generation rate $R_n$ and the transmission probability profile $\alpha_n$ for each transmitter $n \in \mathcal{N}$. However, this objective is not achievable with distributed control and only suboptimal solutions can be computed in polynomial time even with centralized algorithms, due to non-concavity of the utility function of each session n as defined through (5)-(14). With this understanding, the next section focuses on distributed solution algorithms with low computational complexity.

Distributed Algorithm

Some embodiments of the present invention may comprise lightweight, asynchronous, and distributed resource allocation strategies by jointly controlling stochastic channel access and regulating data generation rate to maximize the achievable throughput for each session, within a given energy budget, while keeping the radiated energy level within safety limits. One embodiment of the present invention will be referred to as D-ROSA (Distributed Rate cOntrol and Stochastic channel Access). D-ROSA is based on a local best-response strategy. Each transmitter iteratively solves the problem of joint rate control and transmission probability profile adaption based on a local observation of the second order statistics of the aggregate interference at the receiver.

Let $\Upsilon_n = \{(R_n, \alpha_n)\}$ represent the domain set of session $n \in \mathcal{N}$, which consists of all possible combinations of $R_n$ and $\alpha_n$, as defined in (1)-(4). Then, for a given (fixed) transmission profile of all other sessions in $\mathcal{N}/n$, the individual optimization problem of session $n \in \mathcal{N}$ denoted as OPT($\Upsilon_n, U_n$) with $U_n = U_n(R_n, \alpha_n, \alpha_{-n})$, can be represented as Given: $E_n^{max}, E_n^0, P_n^0, \alpha_{-n}$ (15)

maximize $U_n(R_n, \alpha_n, \alpha_{-n})$
$R_n, \alpha_n$ subject to: Transmission constraints: (1)-(3)

Energy constraint: (4)

Then, the distributed best-response-based algorithm can be formalized, where SOL(Y,$U_n$) represents the solution set of OPT(Y,$U_n$).

Algorithm 1—D-ROSA based on local best response
Data: $E_n^{max}, P_n^0, E_n^0, \forall n \in \mathcal{N}$
(S.0): Choose any feasible $\alpha_n^{(0)} \in \Upsilon_n$ and set k=0
(S.1): If $\{\alpha_n^{(k)}\}_{n \in \mathcal{N}}$ satisfies some stopping criterion, STOP.
(S.2): For each $n \in \mathcal{N}$, solve OPT($\Upsilon_n, U_n(\alpha_n, \alpha_{-n}^{(k)})$).
(S.3): Let $\alpha_n^{(k+1)} \in \text{SOL}(\Upsilon_n, U_n(\alpha_n, \alpha_n^{(k)}))$.
(S.4): Set k←k+1 and goto (S.1).

Implementation Issues.

Algorithm 1 presents a Jacobi version of the distributed algorithm. In practice, different sessions do not need to be synchronized when updating their own transmission probability profile, which may result in a Gauss-Seidel-like implementation of the algorithm. Note that at each iteration in Algorithm 1, each session solves an individual optimization problem formulated in (15), where the transmission probability profile of all other sessions $\alpha_{-n}$ is assumed to be known as input. Since the focus is on fully distributed algorithms without any message exchange among different sessions, then a natural question that arises is: how can each session adjust its transmission probability profile based on the profile of the other sessions?

Each session $n \in \mathcal{N}$ can estimate the statistical effects of aggregate interference from all other sessions in $\mathcal{N}/n$ with transmission profile $\alpha_{-n}$ on its own throughput by recording the first and second moments of the interference level observed at its intended receiver.

Channel fading for ultrasonic communications in intra-body environments can be statistically characterized using a Nakagami distribution function as in (6). The probability density function of the aggregate interference at each measurement instant in $I_n^{tf}(l)$ can be characterized through a Gamma distribution function $$P[I_n^{tf}(l) = x] = \gamma_n^{tfl}(x) = x^{k_n^{tfl}} \frac{e^{-x/\theta_n^{tfl}}}{\Gamma(k_n^{tfl})(\theta_n^{tfl})^{k_n^{tfl}}} \quad (16)$$

where $\Gamma(k_n^{tfl})$ is the gamma function as defined through (6), $k_n^{tfl} = k_n^{tfl}(\alpha_{-n})$ and $\theta_n^{tfl} = \theta_n^{tfl}(\alpha_{-n})$ are the shaping parameters of the Gamma distribution function $\gamma_n^{tfl}(x)$ depending on the transmission profile of all interfering sessions in $\mathcal{N}/n$, i.e., $\alpha_{-n}$. Let $E[I_n^{tf}(l)]$ and $D[I_n^{tf}(l)]$ denote the first and second moment of $I_n^{tf}(l)$ respectively. $k_n^{tfl}(\alpha_{-n})$ and $\theta_n^{tfl}(\alpha_{-n})$ can be represented as $$k_n^{tfl}(\alpha_{-n}) = (E[I_n^{tf}(l)])^2/D[I_n^{tf}(l)], \quad (17)$$

$$\theta_n^{tfl}(\alpha_{-n}) = D[I_n^{tf}(l)]/E[I_n^{tf}(l)], \quad (18)$$

Therefore, to characterize the statistical behavior of the aggregate interference $I_n^{tf}(l)$, any session $n \in \mathcal{N}$ can measure (and record) the corresponding mean and variance. Appendix A contains an experimental verification of the discussed Gamma-distribution-based interference estimation.

Each session $n \in \mathcal{N}$ may periodically transmits an updated estimate of the interference mean and variance back to its transmitter. Then, based on (7)-(12), the transmitter can calculate the outage probability profile $(O_n^{tf}))_{t \in T, f \in F}$ and adjust its data generation rate $R_n$ and transmission profile $\alpha_n$ to maximize its own individual throughput $U_n(R_n, \alpha_n, \alpha_{-n})$ as given in (13) and (14). Since the expression in (14) is still nonconcave, each optimization problem OPT$(\Upsilon_n, U_n)$ is nonconvex. The globally optimal solution of each OPT $(\Upsilon_n, U_n)$ can still be obtained with polynomial-time algorithms.

Each individual optimization problem in OPT$(\Upsilon_n, U_n)$ can be solved by solving an equivalent convex optimization problem.

The objective function $U_n(R_n, \alpha_n, \alpha_{-n})$, with given $\alpha_{-n}$, is a log-concave function. Moreover, all constraints in (1)-(4) are linear constraints, hence the resulting domain set is convex (also bounded and closed). Therefore, maximizing $U_n(R_n, \alpha_n, \alpha_{-n})$ is equivalent to maximizing its logarithm, which is a convex optimization problem, whose globally optimal solution can be solved in polynomial computational complexity. Appendix B contains a proof of the log-concavity of $U_n$.

Globally Optimal Algorithm

The centralized version of the optimization problem solved above can be represented as:

$$\text{Given: } E_n^{max}, E_n^0, P_n^0, \alpha_{-n} \quad (19)$$

$$\underset{R_n, \alpha_n}{\text{maximize}} \ U_n(R_n, \alpha_n, \alpha_{-n})$$

subject to: Transmission constraints (1)-(3)

Energy constraint (4)

Overview of the Solution Algorithm.

As a performance benchmark, a non-heuristic method for global optimization of the problem introduced above is developed based on a combination of the branch and bound framework and the reformulation linearization techniques (RLT). The proposed algorithm searches for a globally optimal solution with predefined precision of optimality $0 < \varepsilon \leq 1$ which can be arbitrarily close to 1. If the globally optimal objective function in (19) is U*, then the algorithm searches for an $\varepsilon$-optimal solution U that satisfies $U \geq \varepsilon U^*$.

The proposed algorithm searches for the optimal solution iteratively. At each iteration, the algorithm maintains a global upper bound $UP_{glb}$ and a global lower bound $LR_{glb}$ on the social objective U in (19) such that $$UP_{glb} \leq U^* \leq LR_{glb} \quad (20)$$

Let $\Upsilon = \Pi_{n \in \mathcal{N}} \Upsilon_n$ represent the Cartesian product of $\Upsilon$ with $n \in \mathcal{N}$, and define the initial search space as the overall domain set $\Upsilon$. As such, the proposed algorithm maintains a set of sub-spaces $\tilde{\Upsilon} = \{\Upsilon_i \subset \Upsilon, i=1, 2, \ldots\}$ where i represents the iteration step of the algorithm. For any $\Upsilon_i$, consider UP(•) and LR(•) as the upper and lower bounds on U in (19) over sub-domain $\Upsilon_i$. We refer to UP($\Upsilon_i$) and LR($\Upsilon_i$) as the local upper bound and local lower bound, respectively. Then, the global upper and lower bounds can be updated as $$UP_{glb} = \max_i \{UP(\Upsilon_i)\}, \quad (21)$$

$$LR_{glb} = \max_i \{LR(\Upsilon_i)\}, \quad (22)$$

If $LR_{glb} \geq \varepsilon \cdot UP_{glb}$, the algorithm terminates and sets the optimal objective U in (19) to $U = LR_{glb}$. Otherwise, the algorithm chooses one sub-domain from $\tilde{\Upsilon}$ and further partitions it into two sub-domains, calculates UP(•) and LR(•), and updates the $UP_{glb}$ and $LR_{glb}$ as in (21) and (22). In this algorithm, $\Upsilon_i$ is selected with the highest local upper bound from $\tilde{\Upsilon}$, i.e., $i = \text{argmax}_i \ UP(\Upsilon_i)$. Based on the update criterion of $UP_{glb}$ and $LR_{glb}$ in (21) and (22), the gap between $UP_{glb}$ and $LR_{glb}$ converges to 0 as the domain-partition progresses. Furthermore, from (20), $UP_{glb}$ and $LR_{glb}$ converge to the globally maximal objective function U*.

The branch-and-bound framework requires that, for given $\Upsilon_i$, the UP($\Upsilon_i$) and LR($\Upsilon_i$) should be possible to calculate. To determine UP(•), relaxation is used, i.e., the original nonlinear non-convex problem into a convex problem is relaxed that is easier to solve using convex programming techniques. For LR(•) a local search is performed for a feasible solution starting from the relaxed solution and the corresponding sum-throughput is set as the local lower bound.

Convex Relaxation.

To relax the social optimization problem in (19) to be convex, all non-convex items must be relaxed, including the non-concave capacity expression in (10) and (12), and the non-concave objective function in (14).

To relax the non-concave expression $C(n,t,f,l)$ in (10), the expression can be rewritten as $$C(n,t,f,l)=\log_2((\delta_n^f)^2+I_n^{tf}(l)+P_n^o h_n^{tf})-\log_2((\delta_n^f)^2+I_n^{tf}(l)) \quad (23)$$

Since the first line of (23) is concave, it is sufficient to only relax the item in the second line. The logarithm can be relaxed with a set of linear constraints. Four lines may be used, one secant and three tangent lines, to approximate the original logarithm function. The lower and upper bound of $\hat{I}_n^{tf}(l) \triangleq (\delta_n^f)^2+I_n^{tf}(l)$ can be calculated with given range of $\alpha_m^{tf}$ for each interfering session $m \in \mathcal{M}/n$ in a specific sub-domain. The relaxation error $\Delta \log(\hat{I}_n^{tf}(l))$, defined as the gap between the relaxed value and the real value of the logarithm function, tends to zero as the sub-domain partition goes.

To relax the non-concave objective function in (19), a new variable may be introduced: $\hat{P}_n^{dly} \triangleq (R_n, \alpha_n, \alpha_{-n})$. Then, the individual objective function in (14) can be rewritten as $U_n(R_n, \alpha)=R_n(1-P_n^{err})+R_n\hat{P}_n^{dly}$, where the first item in the right-hand side is linear while the second item can be relaxed using the RLT. To this end, let $UPR(\hat{P}_n^{dly})$, $UPR(R_n)$, and $LWR(\hat{P}_n^{dly})$, $LWR(R_n)$ represent the upper and lower bounds of $\hat{P}_n^{dly}$ and $R_n$, respectively, with given sub-domain $Y_j$. Further, another new variable may be introduced: $\psi_n=R_n\hat{P}_n^{dly}$. Then, the non-convex item $R_n\hat{P}_n^{dly}$ can be relaxed by substituting $\psi n$ into the following four linear constraints, $$(UPR(\hat{P}_n^{dly})-\hat{P}_n^{dly})(UPR(R_n)-R_n) \geq 0, \quad (24)$$

$$(UPR(\hat{P}_n^{dly})-P_n^{dly})(R_n-LWR(R_n)) \geq 0, \quad (25)$$

$$(\hat{P}_n^{dly}-LWR(\hat{P}_n^{dly}))(UPR(R_n)-R_n) \geq 0, \quad (26)$$

$$(\hat{P}_n^{dly}-LWR(\hat{P}_n^{dly}))(R_n-LWR(R_n)) \geq 0. \quad (27)$$

Since $P_n^{dly}(R_n, \alpha_n, \alpha_{-n})$ defined in (13) is a monotonic function with $R_n-C_n(\alpha_n, \alpha_{-n})$ the above upper and lower bounds $UPR(\hat{P}_n^{dly})$ and $LPR(\hat{P}_n^{dly})$ can be calculated by solving linear optimization problems.

Simulation Results

In this section, the performance of D-ROSA is evaluated in terms of throughput, convergence and optimality through extensive simulation results. Some key simulation parameters are summarized in Table 2.

TABLE 2

Simulation Parameters

| Para. | Physical Meaning | Value |
|---|---|---|
| | Communication area | 40 × 40 × 60 (cm³) |
| β | Number of nodes | 4, 8, 6, 10, 20, 50 |
| | Amplitude attenuation coefficient | 0.1 (ultrasonic propagation in blood) |
| F = ℱ | Number of sub-channels | 1, 2 |
| T = 𝒯 | Number of time slots in a frame | 1, 3, 4, 5, 7, 9, 11 |
| $R_n$ | Data generation rate | 2, 4, 6, 8, 10, 30, 50, 80, 110 (kbit/s) |
| B | Sub-channel Bandwidth of | 50 (kHz) |
| $L_n$ | Packet Length | 100 (bit) |
| $T_{slt}$ | Time slot duration | $0.5 \times 10^{-3}$ (s) |

For performance comparison, three alternative distributed algorithms were implemented: i) D-ROSA based on single-time-slot optimization (Single Slot), ii) D-ROSA without rate control (WoRC), and iii) a combination of the previous two (Single Slot & WoRC). To provide an upper-bound performance benchmark for D-ROSA, a centralized solution algorithm (referred to as C-ROSA) was implemented with optimality precision $\varepsilon=95\%$. All results are obtained by averaging over 100 independent simulations.

Figure 3:
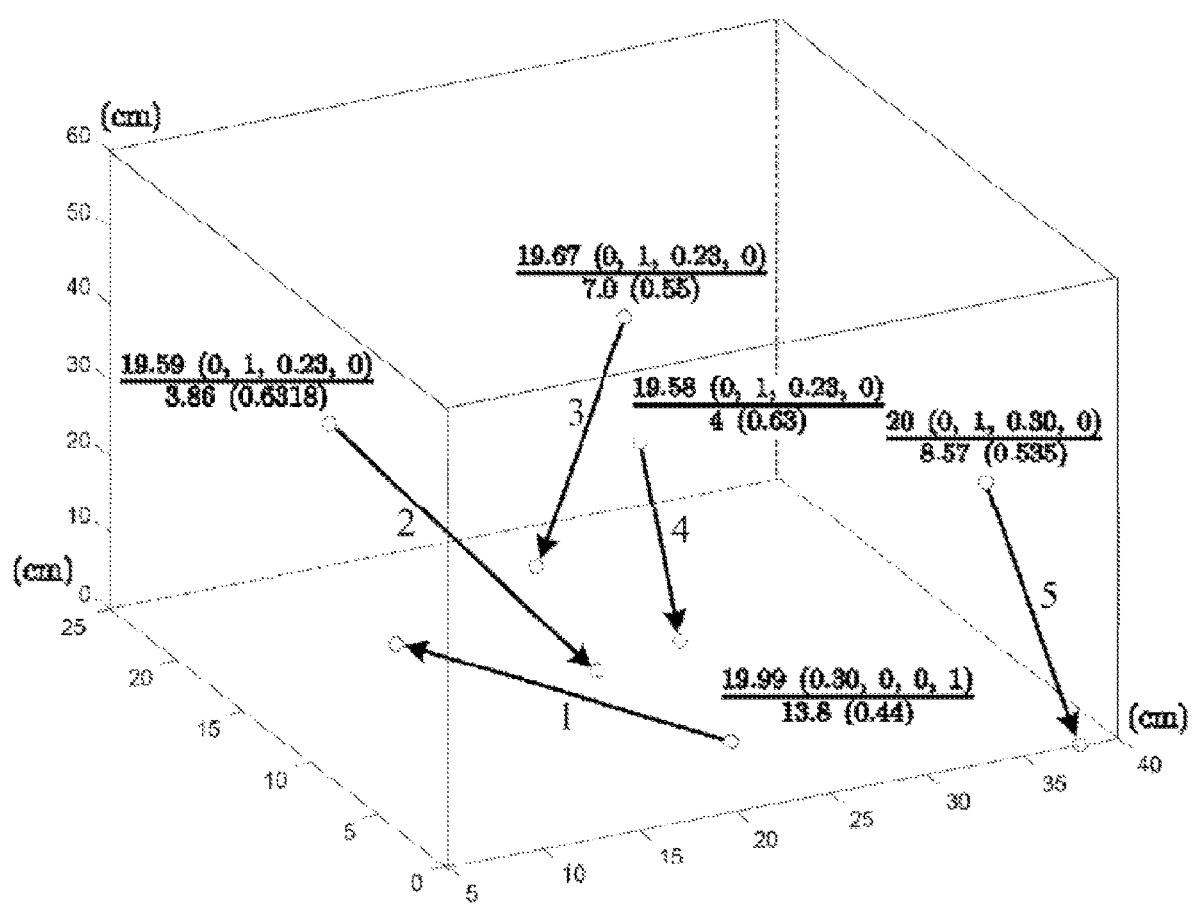
FIG. 3 is an illustration of a five-session I-BWAN according to one embodiment of the present invention.

First, the effect of multislot joint optimization on the individual throughput performance for a five-session I-BWAN is shown in FIG. 3. Significant throughput gains can be obtained by D-ROSA compared with single slot-based channel access (Single Slot). For example, a 5× throughput gain is obtained by session 2. For session 2, a throughput of 19.59 kbit/s is achieved by transmitting with probability 1 and 0.23 in the second and third time slot in each frame, while keeping silent in the first and forth (as indicated in the numerator in the figure). In the single-slot optimization, the session chooses to access the channel with probability 0.6318 in every time slot, and as a result, only 3.86 kbit/s can be achieved. By averaging over the five sessions, a 3.3× throughput is achieved by D-ROSA. One may avoid interference by adding a guard band to each time slot. However, this framework leads to fully distributed solutions, while some approaches in the prior art need global network information, and hence are not suited for fast time-varying networks.

Figure 4:
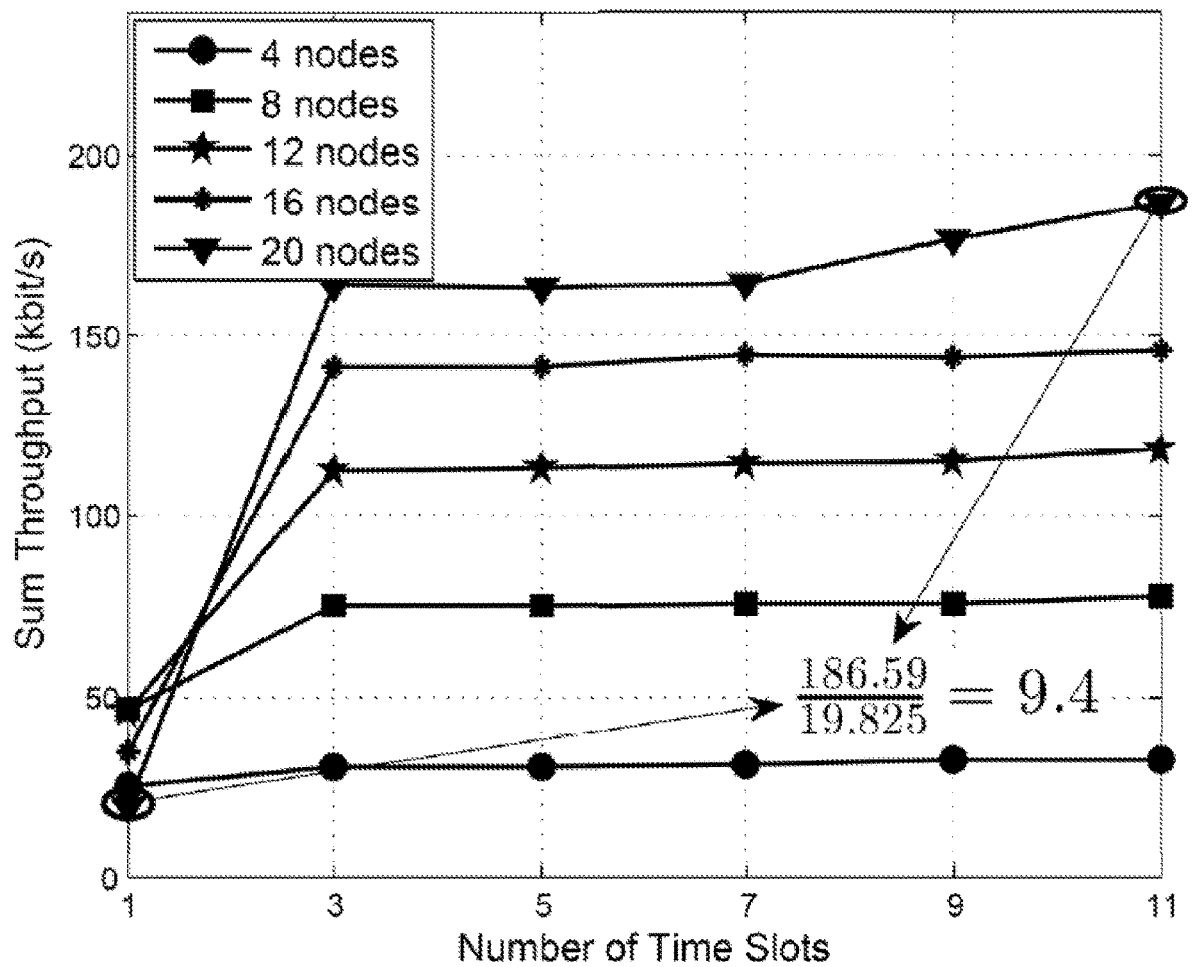
FIG. 4 is a graph showing throughput gains realized by one embodiment of the present invention.

The effect of multi-slot optimization on sum throughput is further shown in FIG. 4, with T varying from 1 to 11 in steps of 2. By comparing the case T=3 with T=1, D-ROSA always obtains throughput gains. Also, in a I-BWAN with a moderate number of nodes, e.g., 4-16 in FIG. 4, jointly optimizing more than three time slots may only slightly increase the sum throughput. In a network with little or moderate interference, a lower number of time slots is sufficient to provide the degrees of freedom needed by the involved sessions to avoid creating excessive interference to one another. An extreme case is the single-session network without interference, where there is little need for the session to perform multi-slot joint optimization. The benefit is more obvious in a high interference network, e.g., in a 20-node I-BWAN, where a maximum 9.4× throughput gain can be achieved by jointly optimizing over 11 time slots.

Figure 5:
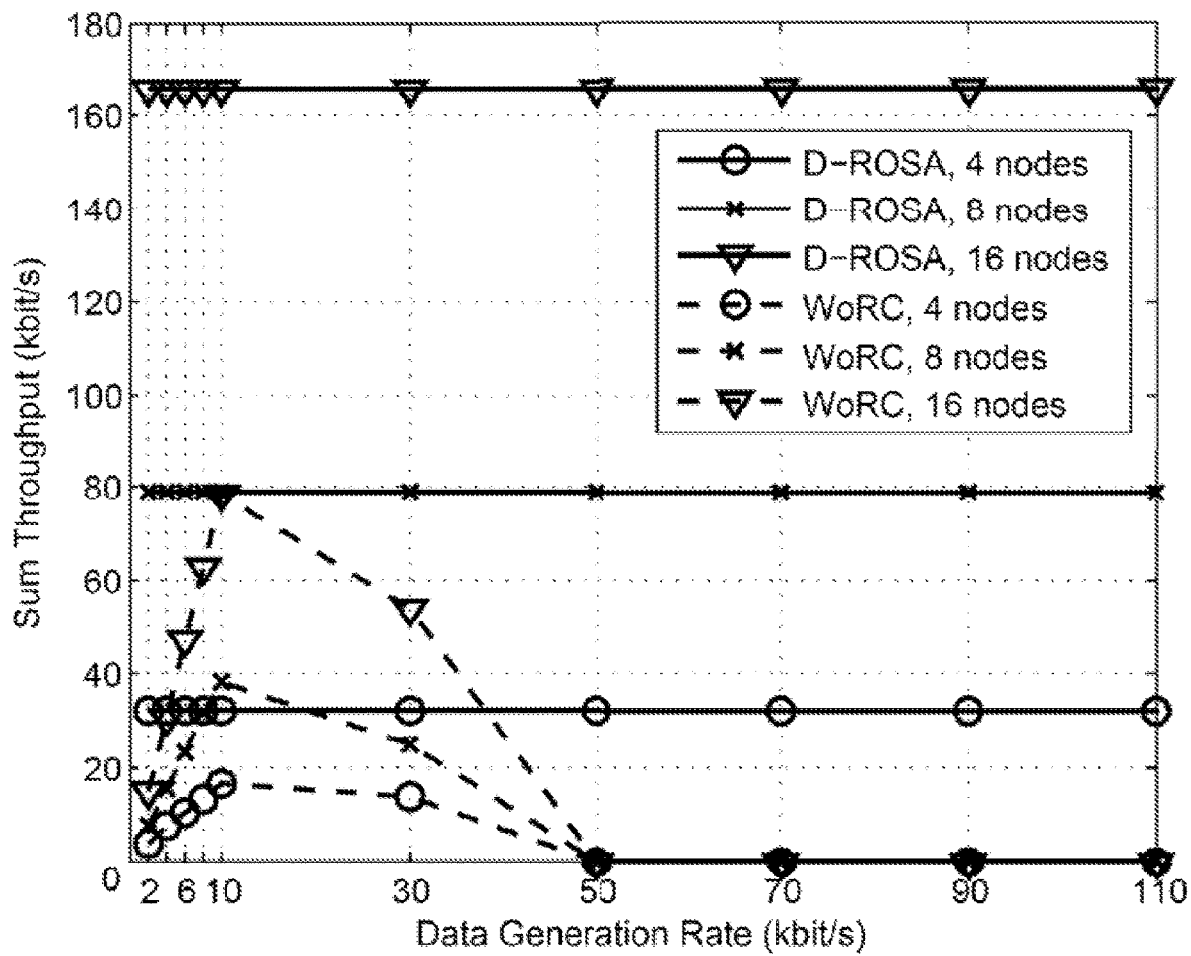
FIG. 5 is a graph showing the impact of rate control on sum throughput realized by one embodiment of the present invention.

The impact of rate control on the sum throughput is shown in FIG. 5, with 4, 8 and 16 nodes, and data generation rate $R_n$ fixed to different values from 0 to 110 kbit/s (for the algorithm WoRC). Compared with D-ROSA, the sum throughput of WoRC degrades considerably once the data generation rate $R_n$ is fixed to a given value for each session. While smaller values of $R_n$ directly degrade the sum throughput, injecting too much data into the network leads to a more congested queue and also less energy available for data transmission with the total energy constraint in (4). Note that, results in FIG. 5 are averaged over 100 simulations by varying the network topology. For a given specific I-BWAN, if the rate $R_n$ can be carefully tailored, e.g., fixed to the optimum, then the resulting throughput of WoRC will coincide with D-ROSA. Doing so however is less flexible in practice for dynamic networks. For example, to measure in real-time specific blood components (e.g., the level of glucose) or to monitor certain tissues for micro-range and even multi-view imaging, a set of implanted sensors would need to cruise within a certain body area along the blood vessel to conduct multi-point measurements. In this case, it would be very difficult to determine the optimal sampling rate in advance.

Figure 6:
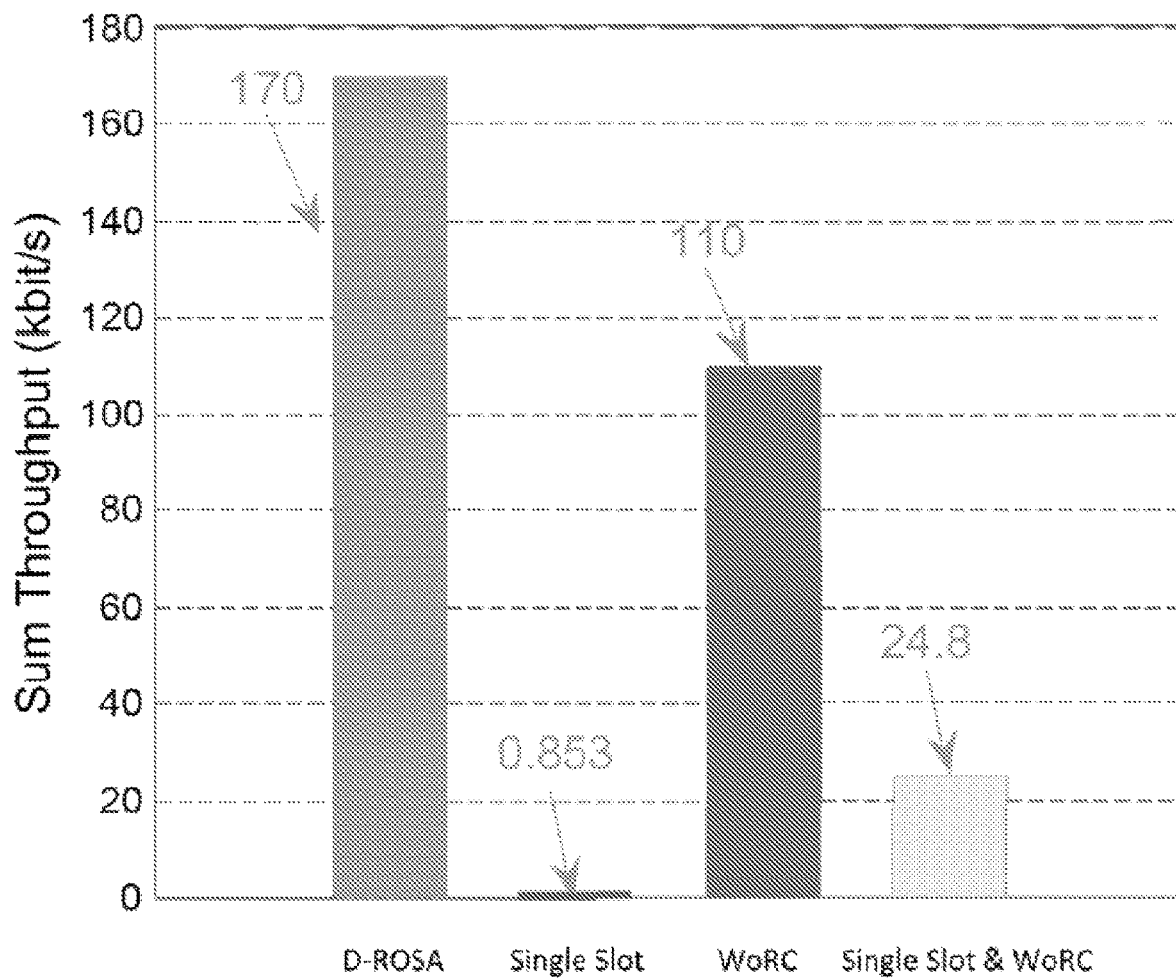
FIG. 6 is a graph showing the sum throughput achieved by four distributed algorithms (D-ROSA, Single Slot, WoRC, Single Slot & WoRC)
Figure 7:
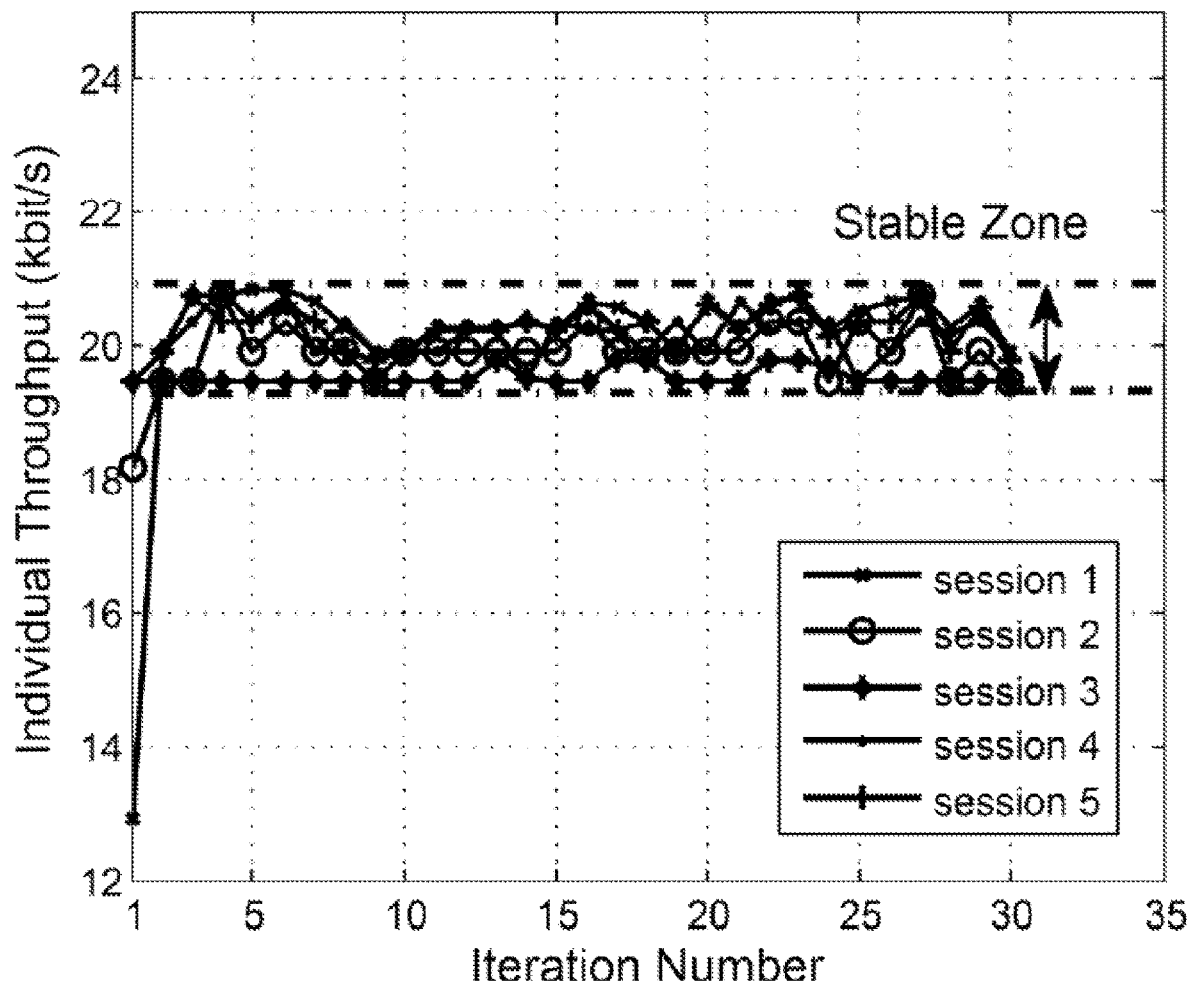
FIG. 7 is a graph showing the convergence and optimality properties of one embodiment of the present invention.
Figure 8:
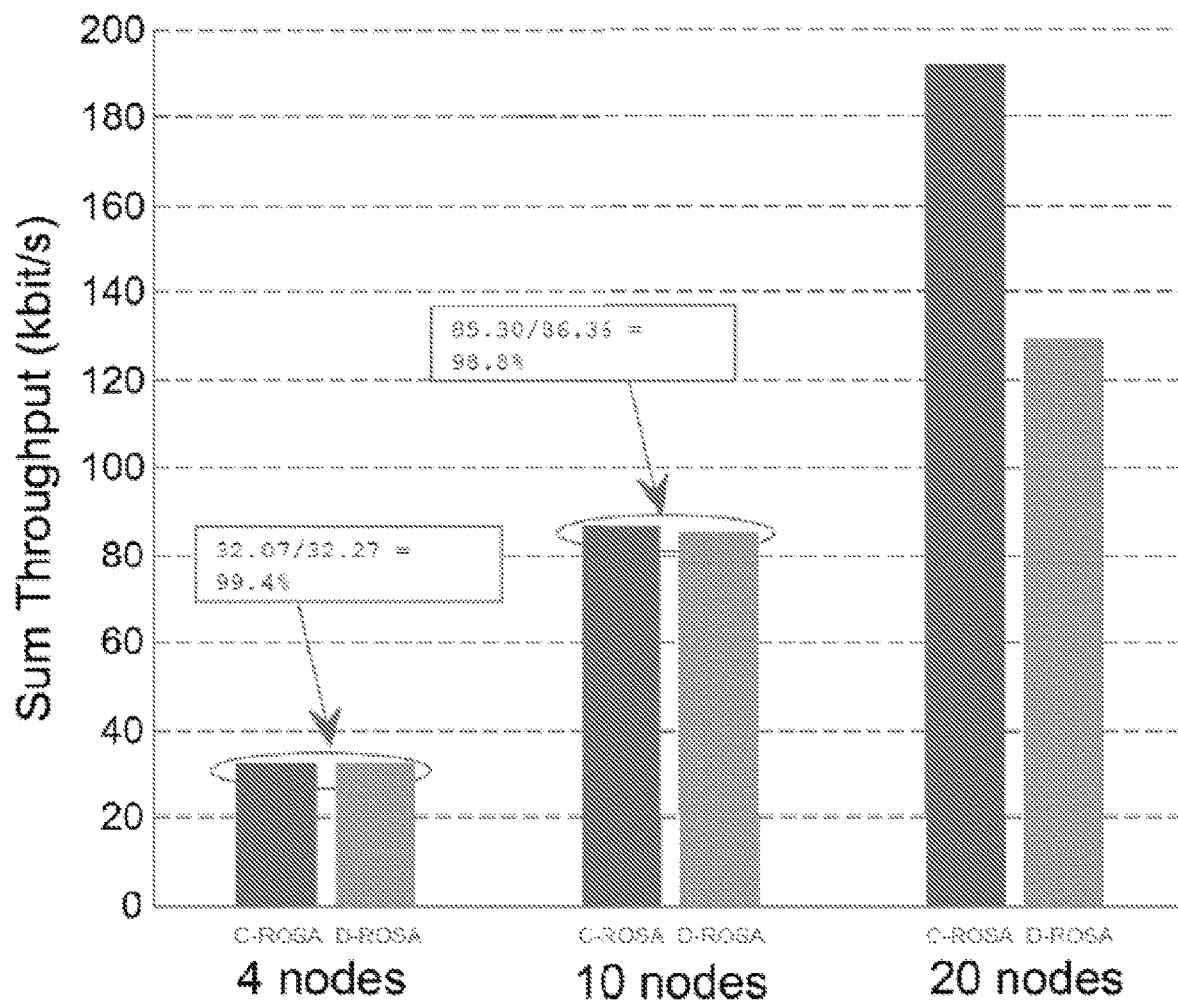
FIG. 8 is a graph showing the convergence and optimality properties of one embodiment of the present invention.

In FIG. 6, the sum throughput achieved by the four distributed algorithms (D-ROSA, Single Slot, WoRC, Single Slot & WoRC) is compared in a 50-node network. While, D-ROSA outperforms all the others, it is somewhat surprising that the throughput achieved by Single Slot can be much worse than that of Single Slot & WoRC. This implies that, in a highinterference network, rate control should be applied together with multi-slot optimization, or otherwise each session will inject large amounts of data into the network to optimize its own individual throughput, while the other sessions have no way to avoid the resulting high interference based on single-slot optimization only. Finally, convergence and optimality properties of D-ROSA are shown in FIG. 7 and FIG. 8 respectively. FIG. 7, illustrates that D-ROSA can quickly converge to a stable zone (always within several iterations in the tested instants). FIG. 8 shows that D-ROSA achieves nearly-optimal sum throughput in I-BWANs with a moderate number of nodes. For example, in 10-node I-BWANs, 98.8% of the global optimum can be achieved by D-ROSA. Results also indicate that the performance gap between D-ROSA and C-ROSA can be considerable when the number of nodes is large, e.g., less than 70% of the optimum can be achieved. Note that this can be achieved in a distributed way and with no message exchange. Cooperative strategies requiring message exchange among different sessions, can partially fill this gap. However, for low densities of nodes that are envisioned in most practical applications, lightweight strategies with minimal message exchange like D-ROSA seem to be more appealing.

APPENDIX A. INTERFERENCE MODEL VALIDATION

First, with given transmission probability profile $\alpha_{-n}$, the expressions for the two shaping parameters $k_n^{tf}(\alpha_{-n})$ and $\theta_n^{tf}(\alpha_{-n})$ are derived. This can be conducted by deriving the mean and variance of $I_n^{tf}(l)$, as denoted as $E[I_n^{tf}(l)]$ and $D[I_n^{tf}(l)]$, respectively. From (5), (6), and (7), $E[I_n^{tf}(l)]$ can be expressed as:

$$E[I_n^{tf}(l)] = E[\Sigma_{m \in \mathcal{N}/n} P_m^0 h_{nm}^{tf} \hat{\alpha}_m^{tf}(n,t,l)] = \Sigma_{m \in \mathcal{N}/n} P_m^0 H_{nm}^{tf} \Omega \alpha_m^{tf}(n,t,l). \quad (28)$$

Similarly, the variance $D[I_n^{tf}(l)]$ can be expressed as:

$$D[I_n^{tf}(l)] = D\left[\sum_{m \in \frac{\mathcal{N}}{n}} P_m^0 h_{nm}^{tf} \hat{\alpha}_m^{tf}(n,t,l)\right] = \Sigma_{m \in \mathcal{N}/n} (P_m^0 H_{nm}^{tf} \alpha_m^{tf}(n,t,l)\Omega)^2 \frac{1}{\omega} \quad (29)$$

where $\Omega$ and $\omega$ in (28) and (29) are the spreading and shaping parameters of the Nakagami distribution function as given in (6).

Figure 9:
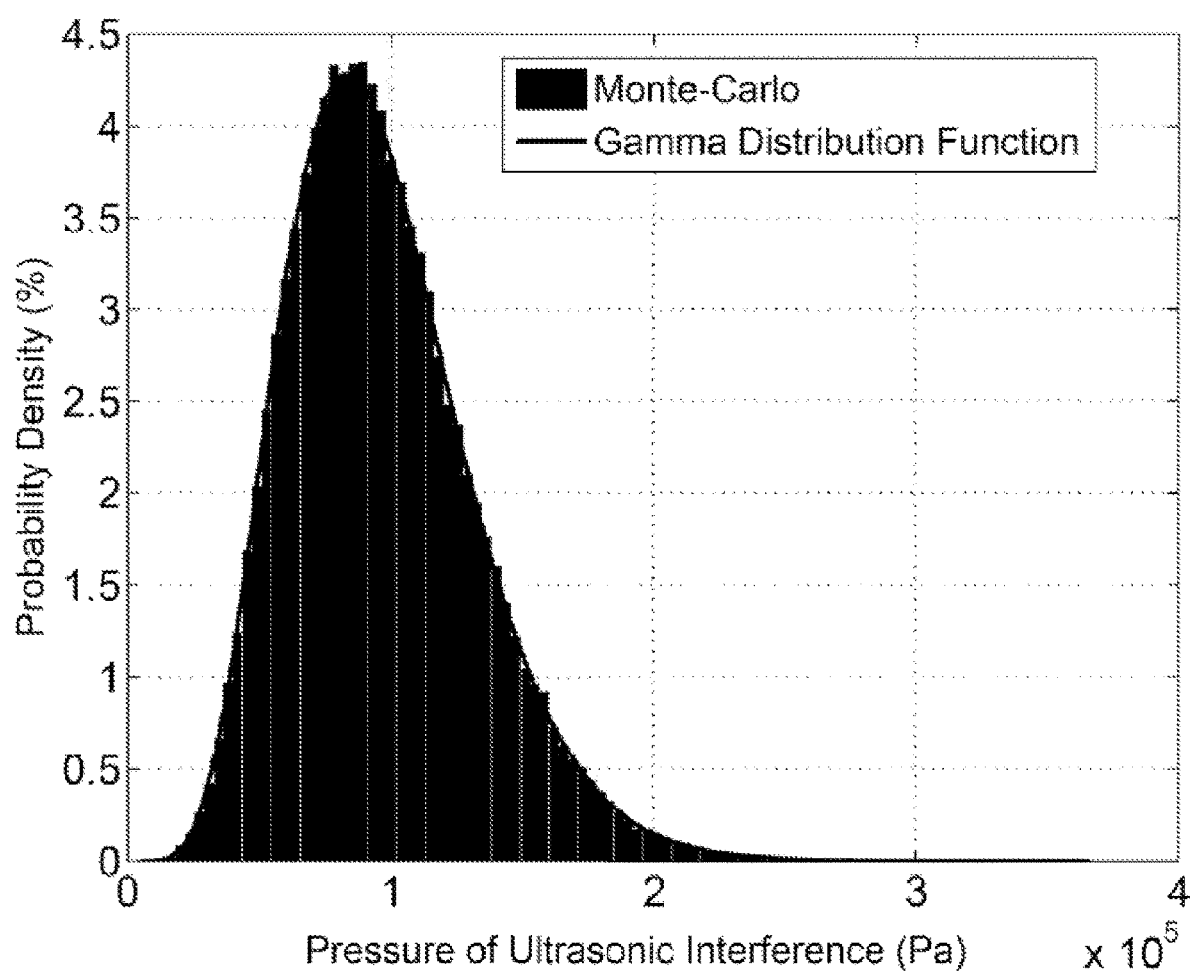
FIG. 9 is a graph of Monte Carlo simulations used to validate the Gamma-function based interference model used in one embodiment of the present invention.

Expressions of $k_n^{tf}(\alpha_{-n})$ and $\theta_n^{tf}(\alpha_{-n})$ can be derived according to (17) and (18). A validation of the Gamma-function based interference model based on Monte-Carlo simulations is shown in FIG. 9. The model fits actual interference very well.

APPENDIX B. PROOF OF LOG-CONCAVITY

Define $\bar{U}_n \triangleq \log(U_n(R_n, \alpha_n, \alpha_{-n}))$, then $\bar{U}_n$ only needs to be a concave function with $R_n$ and $\alpha_n$, with given $\alpha_{-n}$. To this end, $\bar{U}_n$ is rewritten as Since the first and second items in the right-hand side of (30) are linear, only need to show that the third item denoted in the box must be shown to be concave.

Let $y(R_n, \alpha) = C_n(\alpha_n, \alpha_{-n}) - R_n$ then it can be proven, by deriving the second-order derivative of the boxed item is a concave function of y. Moreover, from (11) and (12), with given $\alpha_{-n}$, $y(R_n, \alpha_n, \alpha_{-n})$ is an affine function of $R_n$ and $\alpha_n$. Then, based on the fact that composition with an affine mapping preserves convexity of function, it is shown that the boxed item is a concave function of $R_n$ and $\alpha_n$.

Testbed Validation.

The effectiveness of the proposed algorithm was tested by implementing it on a ultrasonic software-defined testbed. The experiment comprises two ultrasonic nodes that communicate through a human-kidney phantom. Two ultrasonic transducers are located on opposite sides of the phantom at a distance of 10 cm. Time is divided in slots of 100 ms each, and each session can transmit at most one packet of 96 bytes per time slot. At the physical layer, an orthogonal frequency-division multiplexing (OFDM) transmission scheme was implemented. The number of total subcarriers were set to 64, of which 48 are actually used for data transmission, over a bandwidth of approximately 200 kHz centered around 5 MHz, i.e., the central frequency of the ultrasonic transducer in use. The cyclic prefix is set to 16 samples. Each subcarrier is BPSK-modulated. This results in a physical layer data rate of approximately 120 kbit/s.

To guarantee repeatability of the experiments, interference was generated from co-located transceivers by artificially injecting interference at the transmitter, and multiplying each session for a stochastic component that follows a Nakagami distribution. A maximum of five concurrent interfering sessions were considered. In each time slot, each session transmits with a probability $p \in \{0.35, 0.5, 0.65, 0.8\}$. In particular, the interference pattern repeats every four time slots and follows this set of probabilities $p \in \{0.35, 0.5, 0.65, 0.8\}$. The number of jointly optimized time slots, referred to as time frame, from 1 to 9, and the number of packets available in each session queue that need to be transmitted within a time frame is set to 3.

The experiment is divided in two stages. In the first stage, the transmitting node transmits in consecutive time slots while the receiver estimates the corresponding packet drop rate for each time slot. The estimate is sent to the transmitter, that decides accordingly the optimal transmission schedule. In the second stage, the transmitting node transmits the 3 packets in queue in each time frame according to the optimal transmission schedule obtained. At the receiver, the performance of the resource allocation strategy is evaluated in terms of packet drop rate (or packet delivery ratio).

Figure 12:
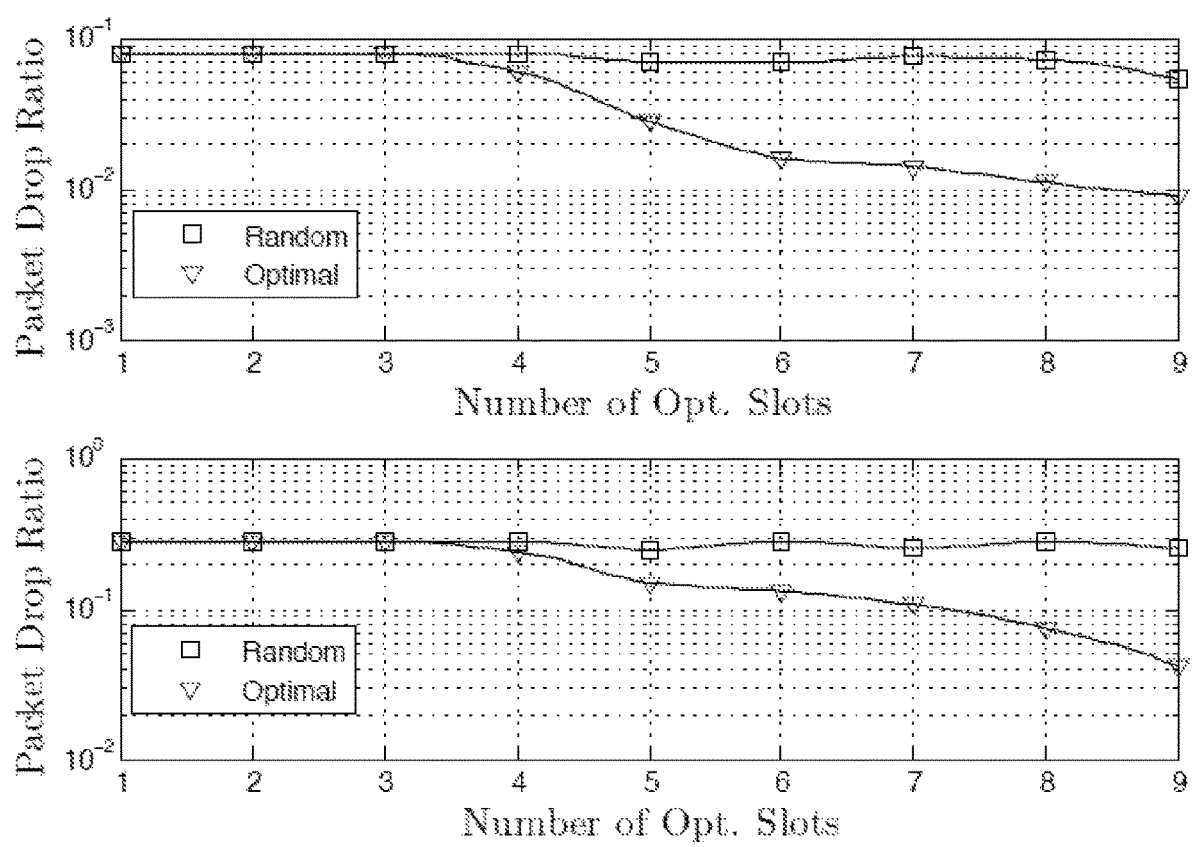
FIG. 12 is a set of charts showing packet drop ratio against the number of jointly optimized time slots according to one embodiment of the present invention.

In FIG. 12, the packet drop rate is plotted against the number of jointly optimized time slots. Two scenarios with different interference levels, i.e., SINR=13 dB in FIG. 12 (top) and SINR=10 dB in FIG. 12 (bottom) are considered. For comparison, D-ROSA is compared with a random channel access, where the transmitting node selects randomly three time slots in a time frame to transmit. The resulting packet drop ratio consistently decreases as more time slots are jointly considered. When jointly considering 9 time slots, up to 10 times lower packet drop rate can be $$\bar{U}_n = \log(R_n(1 - P_n^{dly}(R_n, \alpha_n, \alpha_{-n}) - p_n^{err})) = \log(R_n) - (C_n(\alpha_n, \alpha_{-n}) - R_n)T_n^{th}/L_n + \boxed{\log\left((1 - p_n^{err})e^{(c_n(\alpha_n, \alpha_{-n}) - R_n)\frac{T_n^{th}}{\Delta t}} - 1\right)} \quad (30)$$

achieved compared to random channel access in the case of SINR=13 dB, while 6 times lower than for SINR=10 dB.

EXEMPLARY EMBODIMENT

Figures 10, 11:
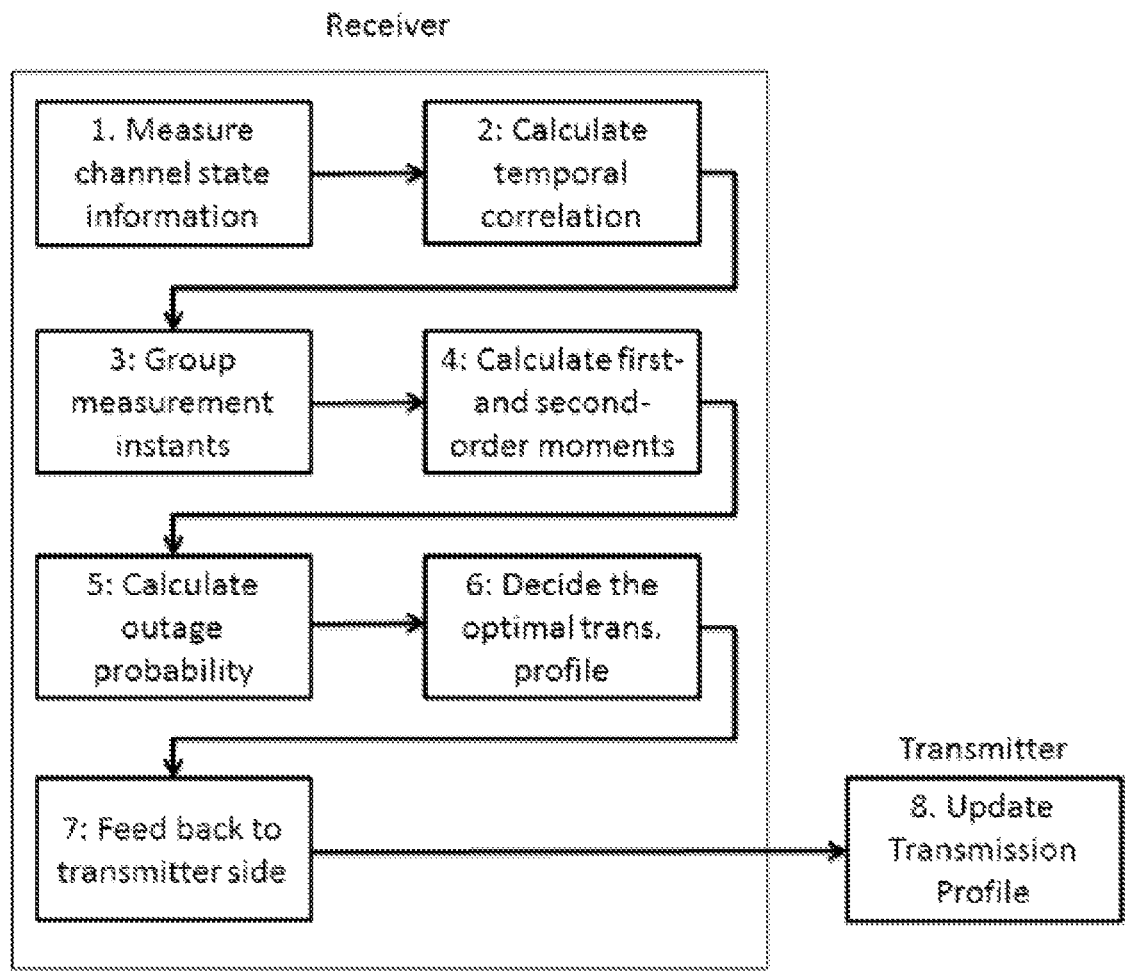
FIG. 10 is a flowchart depicting a method embodiment of the present invention.
FIG. 11 is a diagram of a data packet used in one embodiment of the present invention.

FIG. 10 provides a flowchart illustrating one embodiment of the present invention. In this section, variables are defined as follows:

Given for each transmitter-receiver pair:
T: The number of jointly optimized time slots, i.e., in a time slot group
$\tau$: The number of time slot groups in each strategy-updating period
F: The number of available channels
$P_0$: Transmission power
$T_{slt}$: Time duration of a time slot
M: The number channel state measurements in each time slot
$\eta_{th}$: Threshold of temporal correlation
$R_0$: Threshold transmission rate
B: Bandwidth of each channel
$\Omega$: Channel fading parameter
$P_{err}$: Residual transmission error rate
$T_{th}$: Transmission delay threshold
L: Packet length
$\alpha = (\alpha_{tf})_{t=1,\ldots,T}^{f=1,\ldots,F}$: Transmission probability profile
R: Data generation rate
$\mathcal{M}_{tf}$: Set of channel measurements for the t-th time slot and frequency f
$I_{tf}^m$: Interference variable corresponding to the m-th measurement instant in $\mathcal{M}_{tf}$
$\eta_{tf}^{mn}$: Temporal correlation coefficient between $I_{tf}^m$ and $I_{tf}^n$, with m, n∈$\mathcal{M}_{tf}$
$G_{tf}$: The number of measurement groups for $\mathcal{M}_{tf}$
$N_{tf}^g$: The number of measurement instants in the g-th group in $\mathcal{M}_{tf}$, with g∈{1, . . . , $G_{tf}$}
$E_{tf}^g$: First-order moment of the measured data in the g-th group in $\mathcal{M}_{tf}$, with g∈{1, . . . , $G_{tf}$}
$V_{tf}^g$: Second-order moment of the measured data in the g-th group in $\mathcal{M}_{tf}$, with g∈{1, . . . , $G_{tf}$}
$O_{tf}$: Outage probability corresponding to the t-th time slot and channel f
U: Expected throughput
$P_{dly}$: Packet loss rate due to exceeding the transmission delay threshold One embodiment of the present invention is a method for transmitter-receiver pairs used in intra-body communications comprising the following steps:

Step 1: The receiver measures the power of noise-plus-interference at M uniformly spaced instants in each time slot and on each channel, and records the measured data in set $\mathcal{M}_{tf}$ for the t-th time slot and channel f.

Step 2: The receiver calculates the temporal correlation coefficient $\eta_{tf}^{mn}$ between the channel state variables $I_{tf}^m$ and $I_{tf}^n$ for each channel measurement set $\mathcal{M}_{tf}^{mn}$.

Step 3: For each $\mathcal{M}_{tf}$ the receiver puts consecutive measurement instants into different groups so that i) each group contains as many instants as possible, and ii) in each group, the temporal correlation coefficient between the channel state variables at any two instants is greater than the threshold $\eta_{th}$.

Step 4: For each group g∈{1, . . . , $G_{tf}$} of measurement instants associated with $\mathcal{M}_{tf}$, the receiver calculates the first- and second-order moments of the measured data for the first measurement instant, denoted by $E_{tf}^g$ and $V_{tf}^g$, respectively.

Step 5: The receiver calculates by computing a double integral the outage probability $O_{tf}$ as $$O_{tf} = P\left[\sum_{g=1}^{G_{tf}} \frac{T_{slt} N_{tf}^g}{M} C_{tf}^g < R_0\right] \text{ where } C_{tf}^g = B \log_2\left(1 + \frac{P_0 h_{tf}}{I_{tf}^g}\right),$$

with $h_{tf}$ being a Nakagami distributed variable with parameter $\Omega$, and $I_{tf}^g$, a Gamma distributed variable with mean $E_{tf}^g$ and variance $V_{tf}^g$.

Step 6: The receiver decides (by solving a log-convex optimization problem) the optimal data generation rate $R^*$ and the optimal transmission probability profile $\alpha^*$ to maximize the expected throughput U:

$$(R^*, \alpha^*) = \arg\max_{R,\alpha} R(1 - P_{dly} - P_{err}) \text{ where } P_{dly} =$$

$$e^{-(C-R)\frac{T_{th}}{L}} \text{ and } C = \sum_{f=1}^{F} \alpha_{tf}(1 - O_{tf})R_0.$$

Step 7: The receiver feeds back $R^*$ and $\alpha^*$ to the transmitter side. For each transmitter-receiver pair, the receiver needs to send the optimal transmission profile to the corresponding transmitter. As shown in FIG. 11, feedback data packets consist of three components: i) the ID of the intended transmitter sensor node, ii) the optimal data generation rate $R^*$, and iii) the optimal transmission probability profile $\alpha^*$.

Step 8: The transmitter updates the transmission probability profile $\alpha$ and data generation rate R.

Next, the transmitter transmits the data to its receiver and the receiver sends the data to an external monitoring device and/or to an actuator. The actuator may be internal or external. The monitoring device may be, for example, attached to a wristband or located in a medical facility.

Step 1 above may optionally be preceded by steps a) and b) below:

Step a: The transmitter sets the data generation rate R and transmission probability profile $\alpha$ randomly for each t∈{1, . . . , T} and f∈{1 . . . , F}.

Step b: The transmitter generates data at rate R, and transmits following the probability profile $\alpha$ in the next T×$\tau$ time slots. In the meanwhile, the receiver collects channel state information (CSI) following the steps described above.

In one embodiment, each sensor node runs the algorithm on its embedded computing unit. Methods of the present invention can also be adapted to operate with a central node.

The BAN or BSN may monitor and, optionally, regulate, blood pressure, blood oxygen level, respiratory rate, carbon dioxide level, oxygen saturation, heart rate, cardiac output, blood pressure, pulmonary pressure, body temperature, fluid level, brain function, intracranial pressure, blood sugar, etc.

The actuator may be a medicine pump, cardiac regulator, oxygen tank regulator, or other bodily function regulator. In one embodiment, the medicine pump is an insulin pump.

Table 3 lists exemplary ranges and values for many of the aforementioned parameters of one embodiment of the present invention. Although certain ranges and values are listed, the parameters should not be construed to include only those ranges and values.

TABLE 3

| Parameter | Exemplary Range | Exemplary Value |
|---|---|---|
| T | 1 to 20 | 3 |
| $\tau$ | $\geq 1$ | 10 or 100 |
| F | $\geq 1$ | 1, 2, 5, or 10 |
| $P_0$ | 0.1 to 100 mw | 1 mw |
| $T_{slt}$ | 0.1 to 10 ms | 1 ms |
| M | 1 to 10 | 5 |
| $\eta_{th}$ | 0.5 to 1 | 0.7 |
| $R_0$ | Calculated as $\frac{L}{T_{slt}}$ | Calculated as $\frac{L}{T_{slt}}$ |
| B | 1 kHz to 1 Ghz | 50, 100, or 1,000 kHz |
| $\Omega$ | 0 to 1 | Measured Offline |
| $P_{err}$ | 0 to 0.001 | $10^{-3}, 10^{-4}, 10^{-5}$ |
| $T_{th}$ | Specified by the application | Specified by the application |
| L | $\geq 1$ bit | 100, 1,000 bits |

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method for calculating a forward data generation rate and a forward transmission probability profile for communication through biological tissue using ultrasonic pulses, the method comprising:
    measuring, with a receiver, sets of interference values between the receiver and a transmitter, each set of interference values corresponding to one or more instants in a time slot on a communication channel;
    calculating a first order moment and a second order moment for each instant based on the interference values corresponding to the measured instant;
    calculating an outage probability value for each set; and
    calculating the forward data generation rate and the forward transmission probability profile based on the calculated outage probability value and a predetermined threshold transmission rate, a predetermined transmission delay threshold, and a predetermined residual transmission error rate.

2. The method of claim 1, further comprising:
    grouping consecutive interference values within each set of interference values, such that the temporal correlation coefficient between any two values in each group of consecutive interference values is greater than a temporal correlation threshold;
    wherein the first order moment and the second order moment are calculated for each group based on the interference values corresponding to the group; and
    wherein the outage probability value for each set of interference values is calculated based on the calculated first and second order moments of the groups in the set of interference values.

3. The method of claim 2, wherein the temporal correlation threshold is estimated based on packet drop rate.

4. The method of claim 1, further comprising:
    sending, to a transmitter, the forward data generation rate and the forward transmission probability profile;
    receiving data, from the transmitter, using the forward data generation rate and the forward transmission probability profile.

5. The method of claim 4, wherein the forward data generation rate and the forward transmission probability profile are sent in a data packet comprising:
    an identifier of the intended transmitter; the forward data generation rate; and
    the forward transmission probability profile.

6. The method of claim 4, wherein the receiver performs an action based on the received data.

7. The method of claim 1, wherein the receiver is a transceiver, the method further comprising transmitting data using the forward data generation rate and the forward transmission probability profile.

8. The method of claim 7, further comprising the steps of:
    setting a random data generation rate and transmission probability profile for each time slot and communication channel; and
    transmitting data at the randomly set data generation rate and transmission probability profile;
    wherein the setting and transmitting steps occur prior to the measuring steps.

9. The method of claim 1, further comprising recording the sets of interference values in a memory of the receiver.

10. The method of claim 1, wherein the steps of the method are performed using a processor of the receiver.

11. The method of claim 1, wherein the interference values are measured at uniformly spaced instants.

12. The method of claim 1, wherein the interference values are a measurement of power.

13. The method of claim 1, wherein the consecutive interference values are grouped to contain the maximum number of instants.

14. The method of claim 1, wherein the forward data generation rate and the forward transmission probability profiles are calculated using log-convex optimization.

15. The method of claim 1, wherein noise is a component of the interference values.

16. The method of claim 1, wherein the outage probability value is calculated based on the calculated first and second order moments of each measured instant.

* * * * *